(12) United States Patent
Schwartz

(10) Patent No.: US 7,185,551 B2
(45) Date of Patent: Mar. 6, 2007

(54) PIPETTING MODULE

(76) Inventor: H. Donald Schwartz, 147 Front St., Marblehead, MA (US) 01945

( * ) Notice: Subject to any disclaimer, the term of this patent is extended or adjusted under 35 U.S.C. 154(b) by 0 days.

(21) Appl. No.: 10/692,654

(22) Filed: Oct. 24, 2003

(65) Prior Publication Data

US 2004/0231438 A1 Nov. 25, 2004

Related U.S. Application Data

(63) Continuation-in-part of application No. 10/443,350, filed on May 22, 2003, now Pat. No. 6,805,015.

(51) Int. Cl.
*G01N 1/00* (2006.01)
(52) U.S. Cl. .................................. 73/864.16
(58) Field of Classification Search ............ 73/864.13, 73/864.16, 864.17, 864.18, 864.22, 864.23, 73/864.24, 864.25; 422/100; 436/180; 417/486, 417/487, 488
See application file for complete search history.

(56) References Cited

U.S. PATENT DOCUMENTS

| | | |
|---|---|---|
| 1,983,229 A | 12/1934 | Hillier et al. |
| 2,383,324 A | 8/1945 | LeClair |
| 2,396,602 A | 3/1946 | Posch |
| 3,168,045 A | 2/1965 | Sebastiani |
| 3,273,402 A | 9/1966 | Farr |
| 3,333,548 A | 8/1967 | Lyshkow |
| 3,471,079 A | 10/1969 | Myers |
| 3,525,264 A | 8/1970 | Nieglos et al. |
| 3,646,817 A | 3/1972 | Hinchman et al. |
| 3,695,788 A | 10/1972 | Loomans |
| 3,704,080 A | 11/1972 | Cross |
| 3,802,805 A | 4/1974 | Roeser |
| 3,913,787 A | 10/1975 | Dilger |

(Continued)

FOREIGN PATENT DOCUMENTS

DE 56635 3/1891

(Continued)

OTHER PUBLICATIONS

The written specification and drawings of U.S. Appl. No. 60/511,566.*

(Continued)

*Primary Examiner*—Robert Raevis
(74) *Attorney, Agent, or Firm*—Wolf Greenfield & Sacks

(57) ABSTRACT

An air-filled pipette for accurately metering small and large volumes of fluid samples is provided. The pipette has dual resolution capability such that the pipette can accurately aspirate a wide range of sample volumes and deliver them contact-free (touchless). The pipette may include an extension mandrel that reduces air space in a disposable tip within the pipette. The dual resolution capability and/or the extension mandrel also minimize errors associated with the compressibility of air. Multiple pipettes may also be arranged to form a pipetting module for the metering of multiple sample volumes simultaneously and automatically. The pipette includes a channel block having at least one cylindrical passage, that slides up and down over a rod, and a cylinder, with an axially extending passage therethrough, that is sized, shaped and aligned to fit into the cylindrical passage in a dynamic sealing relationship. A method for mixing multiple fluid samples within a pipette tip is also provided.

12 Claims, 23 Drawing Sheets

U.S. PATENT DOCUMENTS

| | | |
|---|---|---|
| 3,933,048 A | 1/1976 | Scordato |
| 3,935,734 A | 2/1976 | Keegan |
| 4,036,064 A | 7/1977 | Hydo |
| 4,061,037 A | 12/1977 | Keegan |
| 4,076,503 A | 2/1978 | Atwood et al. |
| 4,089,624 A | 5/1978 | Nichols et al. |
| 4,090,818 A | 5/1978 | Hope et al. |
| 4,111,051 A | 9/1978 | Tamm et al. |
| 4,133,211 A | 1/1979 | Sarstedt |
| 4,242,058 A | 12/1980 | Zakora |
| 4,255,096 A | 3/1981 | Coker, Jr. et al. |
| 4,279,991 A | 7/1981 | Hagen et al. |
| 4,304,138 A | 12/1981 | Tervamaki |
| 4,449,897 A | 5/1984 | Garrett |
| 4,493,614 A | 1/1985 | Chu et al. |
| 4,566,868 A | 1/1986 | Menzies |
| 4,568,249 A | 2/1986 | Todd |
| 4,580,453 A | 4/1986 | Taylor |
| 4,610,544 A | 9/1986 | Riley |
| 4,679,446 A | 7/1987 | Sheehan et al. |
| 4,682,712 A | 7/1987 | Bohnensieker |
| 4,715,237 A | 12/1987 | Kaempf et al. |
| 4,715,791 A | 12/1987 | Berlin et al. |
| 4,730,992 A | 3/1988 | Ogawa |
| 4,815,978 A | 3/1989 | Mazza et al. |
| 4,905,526 A | 3/1990 | Magnussen, Jr. et al. |
| 4,941,808 A | 7/1990 | Qureshi et al. |
| 4,971,763 A | 11/1990 | Columbus |
| 4,973,450 A | 11/1990 | Schluter |
| 5,366,904 A | 11/1994 | Qureshi et al. |
| 5,897,034 A | 4/1999 | Sewell |
| 5,983,733 A | 11/1999 | Strandberg et al. |
| 6,143,252 A | 11/2000 | Haxo, Jr. et al. |
| 6,161,442 A | 12/2000 | Sgourakes |
| 6,499,364 B1 | 12/2002 | Suovaniemi |
| 6,645,433 B2 | 11/2003 | Homberg et al. |
| 6,773,927 B2 | 8/2004 | Osawa et al. |
| 2005/0135952 A1* | 6/2005 | Bach ..................... 417/487 |

FOREIGN PATENT DOCUMENTS

| | | |
|---|---|---|
| DE | 0546343 | 3/1932 |
| DE | 19708151 A1 | 9/1998 |
| EP | 0349264 A2 | 1/1990 |
| FR | 2323997 | 4/1977 |
| GB | 0556538 | 10/1943 |
| GB | 2346096 | 8/2000 |
| WO | WO 01/57539 A1 | 8/2001 |
| WO | WO 02/07885 A1 | 1/2002 |
| WO | WO 04/105950 A2 | 12/2004 |

OTHER PUBLICATIONS

International Search Report for PCT/US2004/016144.
Written Opinion of International Searching Authority for PCT/US2004/016144.

* cited by examiner

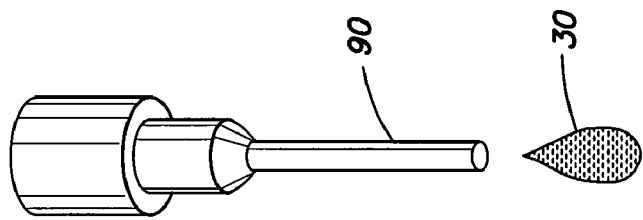
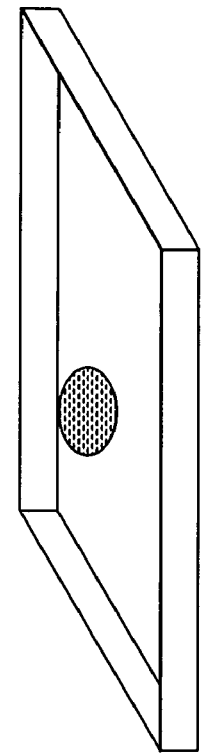
FIG. 2A
FIG. 2B

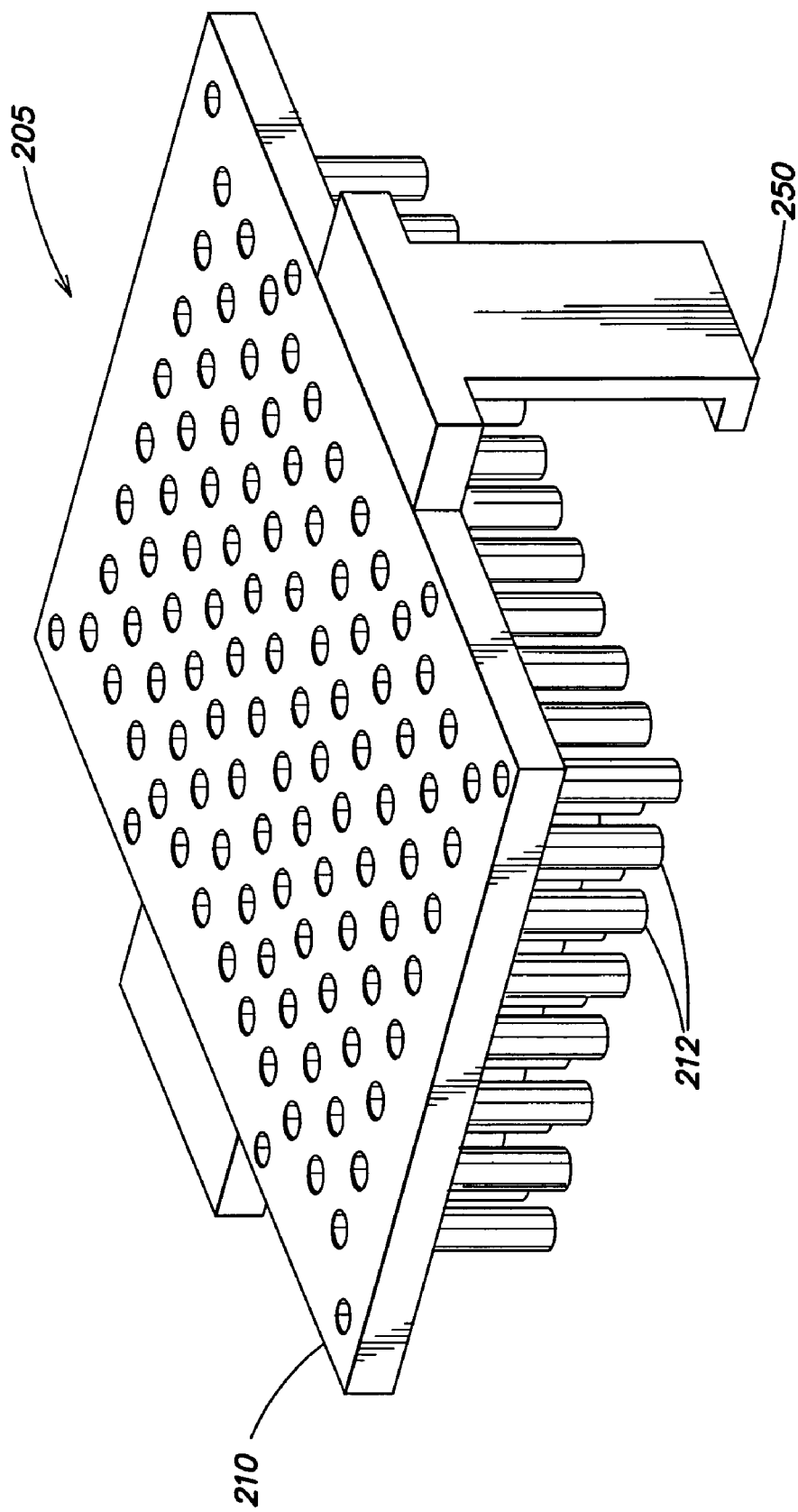

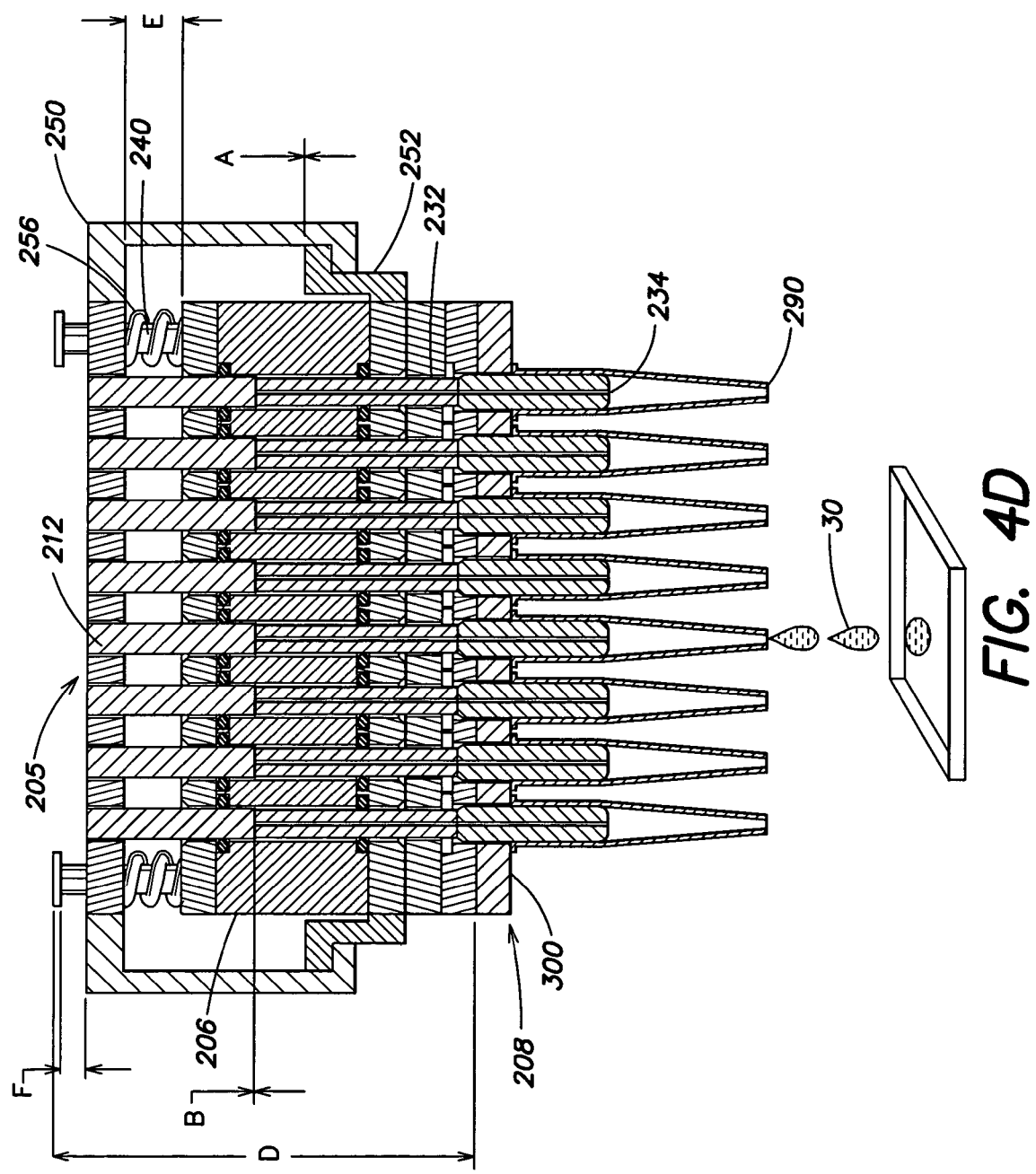

| Cross Section | | Diameter (Inches) | Cross Sectional Area (Square Inches) | Res (uL/inch) | Res (mm/uL) | Flow Max (uL/sec) | Maximum Tip Escape Velocity (meters/sec) for tip diameters (inches) | | | |
|---|---|---|---|---|---|---|---|---|---|---|
| | | | | | | | 0.020 | 0.016 | 0.012 | 0.010 |
| ▨▨ | Hypothetical Fine Resolution Conventional Pipetter | 0.033 | 0.0009 | 14 | 1.8 | 20 | 0.10 | 0.16 | 0.29 | 0.41 |
| ▨▨ | Conventional Pipetter | 0.062 | 0.003 | 50 | 0.51 | 69 | 0.4 | 0.6 | 1.0 | 1.5 |
| | | | | | | | Hanging Drop | | | Blastoff |

FIG. 5A

| Cross Section | Diameter (Inches) | Cross Sectional Area (Square Inches) | Res (uL/inch) | Res (mm/uL) | Flow Max (uL/sec) | Maximum Tip Escape Velocity (meters/sec) for tip diameters (inches) | | | |
|---|---|---|---|---|---|---|---|---|---|
| | | | | | | 0.020 | 0.016 | 0.012 | 0.010 |
| Conventional Pipetter | 0.125 | 0.0123 | 202 | 0.13 | 282 | 1.4 | 2.3 | 4 | 6 |
| PRESENT INVENTION Bulk Mode | 0.184 | 0.026 | 454 | 0.062 | 635 | 3 | 5 | 9 | 13 |
| Differential Mode (fine resolution) | 0.033 | 0.0009 | 14 | 1.8 | 20 | 0.10 | 0.16 | 0.29 | 0.41 |

FIG. 5B

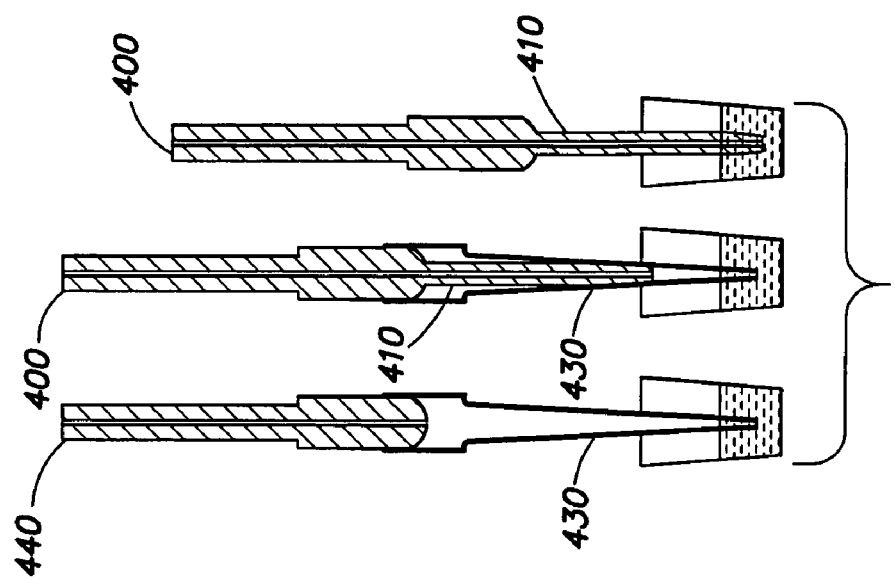
FIG. 10.3
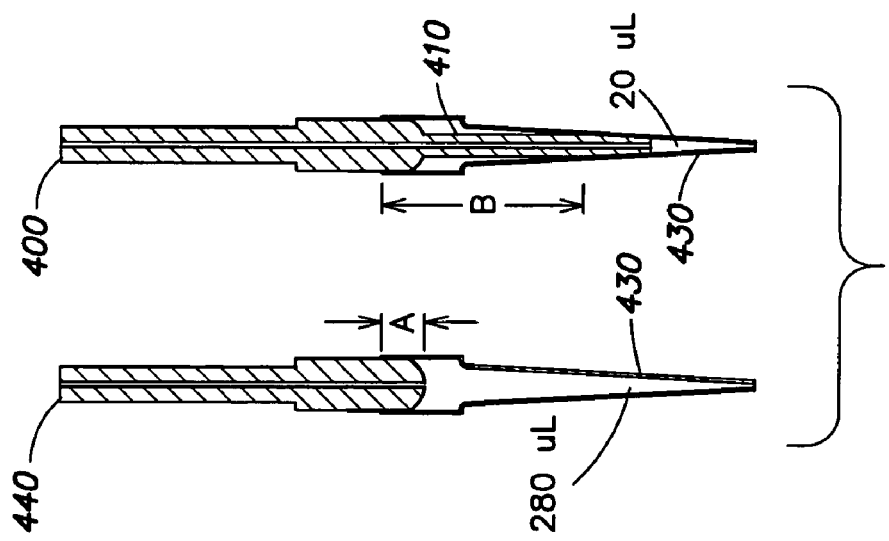
FIG. 10.2
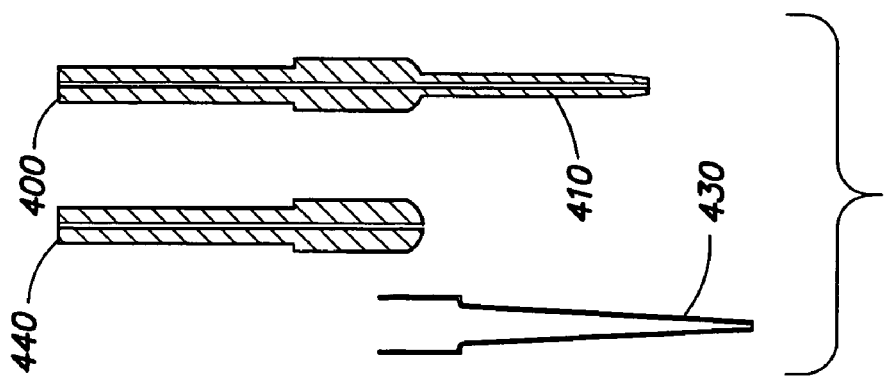
FIG. 10.1

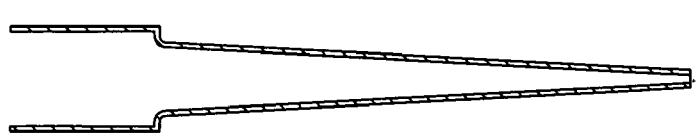
FIG. 11.1
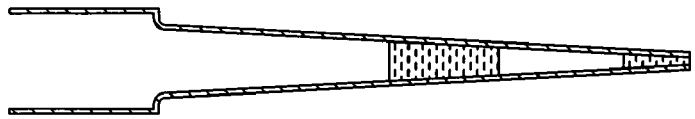
FIG. 11.2
FIG. 11.3
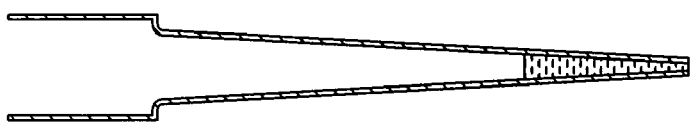
FIG. 11.4

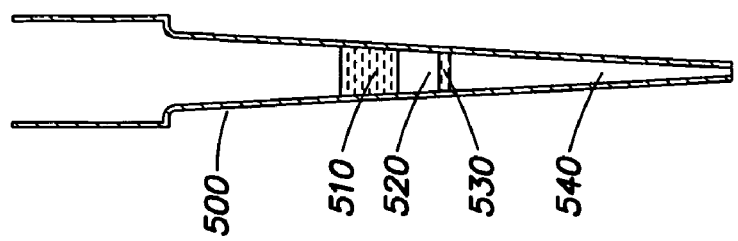
FIG. 12.4
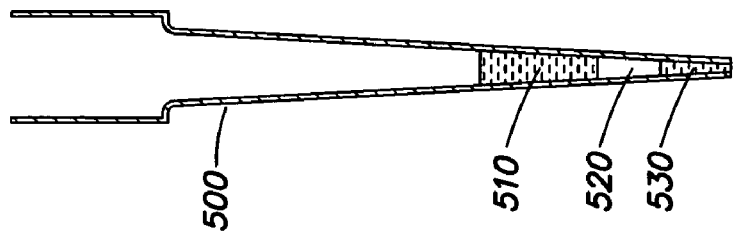
FIG. 12.3
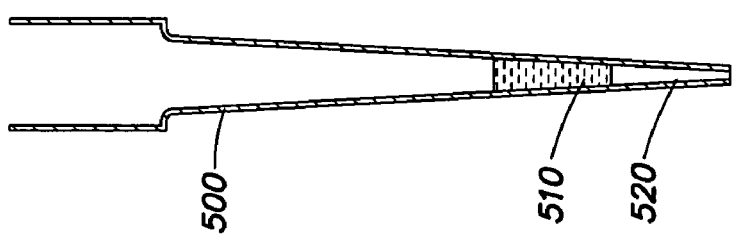
FIG. 12.2
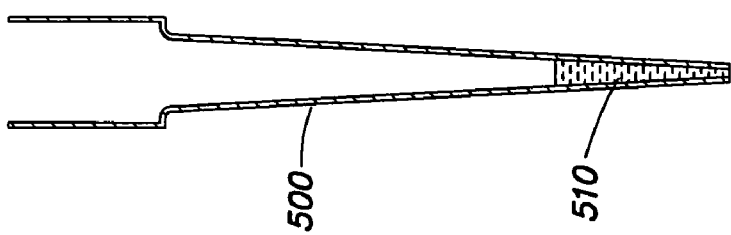
FIG. 12.1

FIG. 12.8
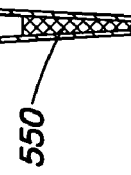
FIG. 12.7
FIG. 12.6
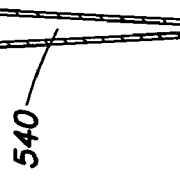
FIG. 12.5

PIPETTING MODULE

RELATED APPLICATIONS

This application claims the benefit under 35 U.S.C. § 120 of U.S. application Ser. No. 10/443,350 entitled "Dual Resolution Syringe," filed on May 22, 2003 now U.S. Pat. No. 6,805,015, which is herein incorporated by reference in its entirety.

BACKGROUND OF INVENTION

1. Field of Invention

The present invention relates to air-filled pipettes which can accurately meter small volumes of fluid and deliver them contact free or touchless. In one embodiment, the pipette has dual resolution capability which enables the aspiration and dispensing of a wide range of sample volumes. In one embodiment, the pipette has an extension mandrel, within the pipette tip, which may be removable, which reduces the internal dead space volume within the pipette tip. The pipette of the present invention may also be capable of metering multiple sample volumes simultaneously and automatically.

2. Discussion of Related Art

Although pipetting technology has been in use for years, there is a demand for a pipette that can accurately meter smaller and smaller sample volumes and deliver the tiny volumes to a receiving container or surface without having to physically contact a surface to wick the sample off of the pipette tip. Further, there is a demand for such a pipetting system that can accurately and simultaneously aspirate and dispense multiple samples at once.

One method of metering small sample volumes involves a liquid-filled system such as the system described in co-pending application Ser. No. 10/443,350. In this system, a relatively incompressible priming liquid assists in aspirating and dispensing a liquid sample by occupying all of the space within the system except for a minimal air space needed to separate the sample and the priming liquid from each other. Although this is an effective and accurate way to meter small sample volumes, the use of a priming fluid generally requires liquid-containing fluid lines between the metering mechanism and the probe tip, and for multi-channel automated systems, this can be messy. Also, bubbles may get into the priming fluid, which may lead to measurement error and inaccuracies.

Therefore, for ease of use, there is a need for a method and apparatus for accurately metering small sample volumes, that does not require a liquid-filled system.

Conventional air-filled systems have been known in the past. However, since air is a very compressible fluid whose density is also very temperature dependent, measurement error may result because the density of the air within the system may vary. In an incompressible fluid metering system, the volume of the sample that is aspirated or dispensed is substantially identical to the volume of internal or priming fluid that is moved. In a compressible fluid metering system, such as an air-filled system, the volume of the sample aspirated or dispensed also tracks the volume of internal or priming fluid that moved, but will not exactly equal it. In a compressible fluid metering system, such as an air-filled system, if the density of the air is altered with the movement of the air, a measurement error of the fluid sample can result. For example, during aspiration, if the air density decreases, the volume aspirated may fall short of the desired volume to be aspirated, or aspiration may fail completely. During dispensing, if the density of the air in the system increases, the measured volume of the fluid sample may be less than the intended volume. In addition, a large volume of low density air can prevent complete dispensing by absorbing the required dispensing force.

Due to these measurement errors, in the past, for a conventional air-filled metering system to maintain reasonable measurement accuracy, the system is limited in volume range. For example, due to the compression associated with an air-filled system, even a 5 microliter sample can not typically be accurately metered with an air-filled pipetting system that is capable of also accurately metering a 50 microliter sample. This is partly because in an air-filled metering system designed for accurately metering a 50 microliter sample, the internal volume of air within the pipette is so much greater than that of the 5 microliter sample. So when a force is applied to the system to meter the sample, the air may compress or expand by as much or more than the volume of the sample. Therefore, when this air-filled system attempts to aspirate or dispense a sample, the air volume will result in a high margin of measurement error. While the percentage of error may be limited by narrowing the range of sample volumes metered with a particular sized system, for versatility reasons, it is advantageous to have an air-filled metering system that can accurately aspirate and dispense a wide range of volumes of samples and reagents. Compounding all of the compressibility problems of air-filled pipettes mentioned above is the fundamental resolution/flow dilemma that the present invention uniquely solves.

Conventional pipettes are also limited in that they only use a single resolution mode to aspirate and dispense fluid samples. The one mode of conventional pipettes does not allow varying resolutions for metering samples. The present invention provides an air-filled pipette system which has fine resolution to aspirate a small sample, and also has the high resolution power to fully dispense the sample from the pipette.

It is an object of the present invention to provide a pipetting system which can accurately meter small sample volumes, yet can also accurately meter a wide range of sample volumes implementing an air-filled system. It is also an object of the present invention to provide a pipetting module which permits the simultaneous metering of multiple sample volumes.

SUMMARY OF INVENTION

The present invention overcomes prior limitations associated with the use of an air-filled pipette. In particular, with the dual resolution capability of the present invention, the pipette can accurately aspirate and dispense a wide range of sample volumes. Further, the present invention helps to increase the accuracy of the measured sample volumes by decreasing the volume of air within the pipette. The volume of air within the pipette is decreased by use of the two resolutions and also by use of a an extension mandrel within the pipette tip.

In one illustrative embodiment of the invention, a pipette is provided with dual resolution capabilities. The pipette comprises a channel block having a cylindrical passage, a rod sized to go in and out of the cylindrical passage, and a cylinder with a passageway therethrough sized to go in and out of the cylindrical passage. The channel block, rod and cylinder define a chamber having a variable volume. A first part of the chamber is variable by relative movement of the channel block relative to the fixed relative positions of the rod and cylinder, and a second part of the chamber is variable by relative movement of the cylinder relative to the fixed relative positions of the rod and channel block.

In another illustrative embodiment, a pipetting module is provided with dual resolution capabilities. The pipetting module comprises a channel block with a plurality of cylindrical passages, a rod plate having a plurality of cylindrical rods sized to move down into and out of the corresponding cylindrical passages, a cylinder plate, having a plurality of cylinders with axially extending passages, sized to pass upwardly into and out of the corresponding cylinder passages in the channel block, with the diameter of the rods and cylinders being different, and a plurality of tips having passages therethrough, extending downwardly from the bottoms of the cylinders.

In another illustrative embodiment, an air-filled pipette for metering volumes of fluid is provided. The air-filled pipette includes a cylinder with an elongated passageway therethrough, a channel concentric with and movable relative to the cylinder defining an air-filled chamber at one end of the cylinder, the cylinder having an outer surface spaced from an inner surface of the channel, a rod positioned and longitudinally movable in and out of the channel, a tip having a passageway therethrough, extending downwardly from the bottom of the cylinder, and an extension mandrel, which may be removable, with a passageway extending therethrough. The mandrel is attached to an end of the cylinder, so that the passageway extending through the mandrel is aligned to correspond with the elongated passageway in the cylinder, and the mandrel reduces the volume within the tip.

A method of metering multiple fluid samples with a pipette including an extension mandrel is provided, and in another embodiment, a method of mixing multiple samples within a pipette tip is provided.

BRIEF DESCRIPTION OF DRAWINGS

The accompanying drawings, are not intended to be drawn to scale. In the drawings, each identical or nearly identical component that is illustrated in various figures is represented by a like numeral. For purposes of clarity, not every component may be labeled in every drawing. In the drawings:

FIGS. 2A–2B illustrates a "hanging drop" and a fully dispensed drop;

FIGS. 3A–3D illustrates perspective views of the different subassemblies of the pipette module;

FIGS. 4A–4D illustrates cross-sectional views of selected positions of the pipette module;

FIGS. 5A–5B illustrate a table comparing one embodiment of the present invention to conventional air pipettes;

FIG. 10 illustrates one embodiment of the extension mandrel filler;

FIGS. 11.1–11.4 illustrate one method for mixing a plurality of aspirated samples sequentially in one tip by means of the Blastoff process;

FIGS. 12.1–12.8 illustrate one method for mixing a plurality of aspirated samples within a pipette tip prior to the Blastoff process.

DETAILED DESCRIPTION

Figure 1C:
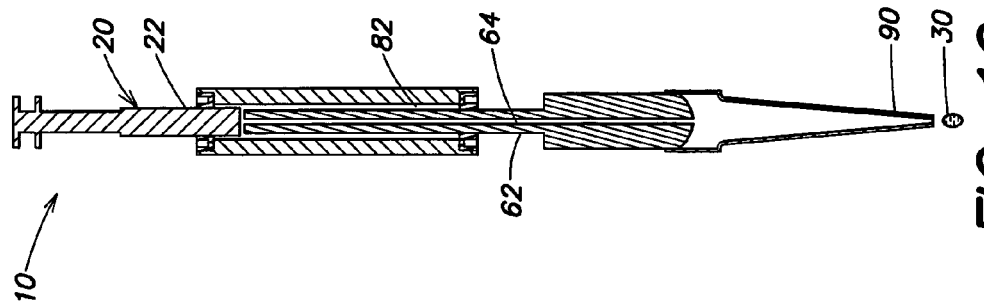
FIGS. 1A–1C illustrates the pipette of the present invention in three selected positions in detail.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Figure 1B:
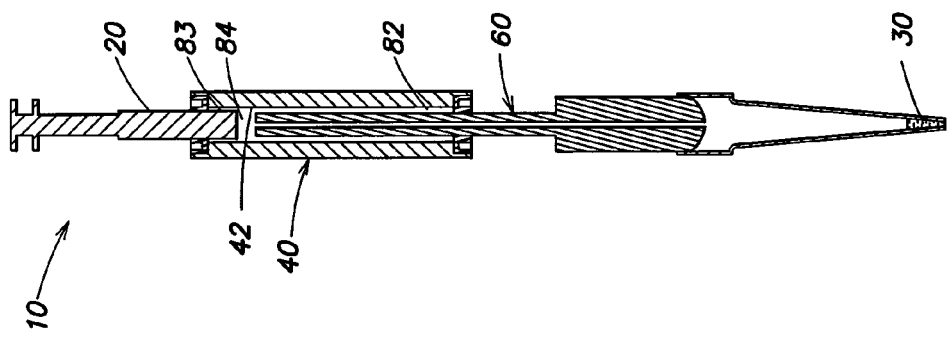
Figure 1A:
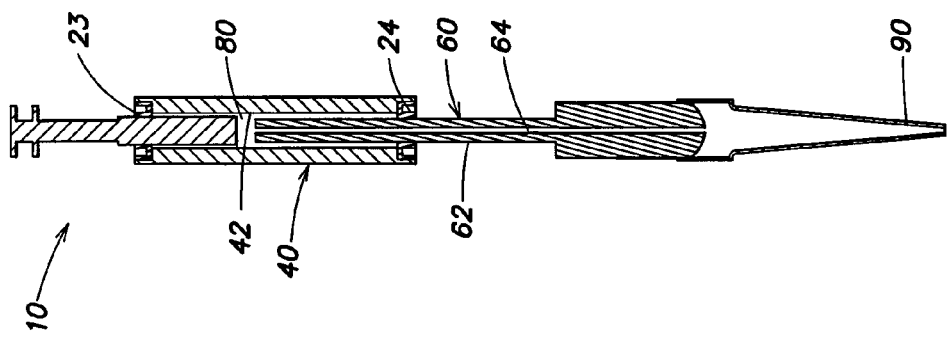

While the present invention typically involves a module of multiple pipettes, one representative pipette of the pipetting module is shown in FIGS. 1A–1C. The pipette 10 comprises a piston 20, a channel 40 concentric with and movable relative to the piston, and a stationary cylinder 60. The channel defines an internal chamber 80 positioned between the piston 20 and the cylinder 60. The volume of the chamber 80 within the channel 40 is variable, relative to the position of both the movable piston 20 and the movable channel 40. The piston is sized and shaped to occupy selected volumes of the movable chamber 80. Although the difference may be slight, the diameter of the piston 20 is larger than the diameter of the stationary cylinder 60. Therefore, the outer surface 62 of the cylinder 60 is spaced from the inner surface 42 of the channel 40, in part defining the volume of the chamber 80. The outer surface 62 of the cylinder is preferably uniformly spaced from the inner surface 42 of the channel 40 to form a portion of the chamber 80. This annular portion 82 thus defines an annular chamber between the outer surface 62 of the cylinder 60 and the inner surface 42 of the channel 40. Other shaped segments, however, are contemplated. This may be achieved by shaping the outer surface 62 other than cylindrical. A second portion 84 of the chamber 80 includes the portion between the end of the piston 20 and the adjacent end of the cylinder 60. In one embodiment, the maximum volume of the first annular portion 82 of the chamber 80 is significantly less than the maximum volume of the second portion 84 of the chamber 80. A multiplying factor between the cross-sectional areas of the first portion 82 and the second portion 84 of approximately 10 to 100 is preferred. The outer surface 22 of the piston 20, is also preferably uniformly spaced from the inner surface 42 of the channel 40 to provide clearance between the piston and the channel as the piston moves in and out of the channel 40. This clearance space defines a third portion 83 of the chamber 80.

The pipette 10 further includes a sealing means 23 which defines an end of the chamber 80 at the end of portion 83 or 84. In one embodiment, the sealing means 23 is a compression seal fixed to the inner surface 42 of channel 40 and is axially movable with the channel 40 relative to the piston 20. A second sealing means 24 defines another end of the chamber 80 at the end of portion 82. In one embodiment, the sealing means 24 is a compression seal fixed to the inner surface 42 of channel 40 and is axially movable with the channel 40 relative to the cylinder 60.

The stationary cylinder 60 includes an elongated passage 64 extending through the cylinder 60, which connects the internal chamber 80 with a pipette tip 90. Fluid (typically air in an air-filled system) flows in and out of the chamber 80 through the passage 64. As the volume of the fluid within the chamber 80 expands and contracts, the fluid in the passage 64 either moves into the chamber 80 or moves out through the passage 64 and through the tip 90.

The volume of the chamber 80 may be varied by movement of the channel 40 with respect to the piston 20 and the cylinder 60. Alternatively, the volume of the chamber 80 may be varied by movement of the piston 20 and the channel 40 with respect to the cylinder 60. Movement of the piston 20 and the channel 40 relative to the cylinder 60 alters the volume in the second portion 84 of the chamber 80, while movement of the of the channel 40 relative to the piston 20 and cylinder 60 alters the volume of the first portion 82 and the third portion 83 of the chamber 80.

The pipette of this invention provides aspiration and ejection or dispensing, of fluids in two resolutions. These two resolutions are discussed at more length in co-pending U.S. application Ser. No. 10/443,350. The movement between FIGS. 1A–1B illustrates Differential Mode, while the movement from FIGS. 1B–1C illustrates Bulk Mode. As shown, in FIG. 1, Bulk Mode is typically used to completely dispense a fluid sample 30 from the tip 90.

Bulk Mode is defined as a coarse (low) resolution/high flow/high volume mode of the pipette. In the Bulk Mode, the channel 40 and the piston 20 move together, causing the volume in the chamber to change. In Bulk Mode, the volume is displaced due to a change in the volume of the second portion 84 of the chamber. In the above described mode, with no measurement errors, the volume displaced is equal to the cross-sectional area of the cylinder multiplied by the vertical displacement of the piston 20 and the channel 40. If the radius of the cylinder is "R3" and the vertical displacement of the channel and the piston is "X", then the volume displaced is equal to $\pi(R3)^2 X$. This is derived from the fact that the volume displaced is equal to the internal cross-sectional area of the channel 40 minus the cross-sectional area of the annular first portion 82 multiplied by the vertical displacement of the piston 20 and the channel 40.

Differential Mode is defined as a fine (high) resolution/low flow/low volume mode of the pipette. In the Differential Mode the channel 40 moves relative to the cylinder 60 and piston 20 and the volume displaced is equal to the volume change in the first portion 82 of the chamber minus the volume change in the third portion 83 of the chamber. This volume change is equal to the difference between the cross sectional areas of the piston and the cylinder multiplied by the vertical displacement of the channel 40. If the piston and channel are cylindrical and the radius of the piston is "R2", the radius of the cylinder is "R3", and the vertical displacement of the chamber 40 is "X", then the displaced volume is equal to $[\pi(R2)^2 - \pi(R3)^2]X$. If there is substantially no clearance space between the inner surface of the channel and the outer surface of the piston (i.e. no third portion of the chamber), the displaced volume is equal to $[\pi(R1)^2 - \pi(R3)^2]X$ where "R1" is the radius of the inner surface of the channel.

Bulk and Differential Mode provide many advantages in the present invention. For example, when in Bulk Mode, the pipette is capable of metering a large volume of fluid very quickly and with a high flow rate. Then, in Differential Mode, the pipette is capable of metering a very precise and accurate small volume of fluid smoothly. Since the pipette is capable of switching back and forth between Bulk Mode and Differential Mode, a wide range of precision and flow rate/volume is obtained with the pipette of the present invention. In one embodiment, the present invention includes a valve to aid in the process of switching between modes. Further, with a valve, the start of an aspiration may occur with approximately no dead space within the chamber. Alternatively, Bulk and Differential Mode may be used to provide an aspiration resolution that differs from the dispensing resolution.

Conventional air pipette systems with enough resolution to pick up a small volume generally cannot provide enough flow velocity to fully expel the fluid sample 30 from the tip 90, resulting in a "hanging drop", illustrated in FIG. 2A. One technique used to remove the drop from the tip is to physically touch the drop off against the bottom or the side of a receiving container or surface. This method may not be very precise and accurate. Another technique is to use a solenoid or bellows to deliver a burst of pressure to knock the drop off. While this method may be effective in the removal of the drop, the velocity of such expulsions tends to be hard to control and the drop can be damaged and broken into fragments, or splattered onto the receiving surface in the process. Therefore, to avoid a "hanging drop", many conventional pipettes are sized to be large enough to fully expel the sample, but such size compromises the aspiration resolution.

FIG. 2B illustrates how the present invention eliminates the "hanging drop" problem. Because it is stepper-motor driven, the present invention can deliver a precisely controlled and even ejection velocity to the drop, using Bulk Mode. This results in complete removal of the sample drop 30 from the tip 90, at a controlled velocity, to ensure that the integrity of the drop is preserved. This is advantageous for analytical techniques that rely on intact genetic fragments or ability of another technology (like a laser or ion stream) to access the intact drop.

Figure 3:
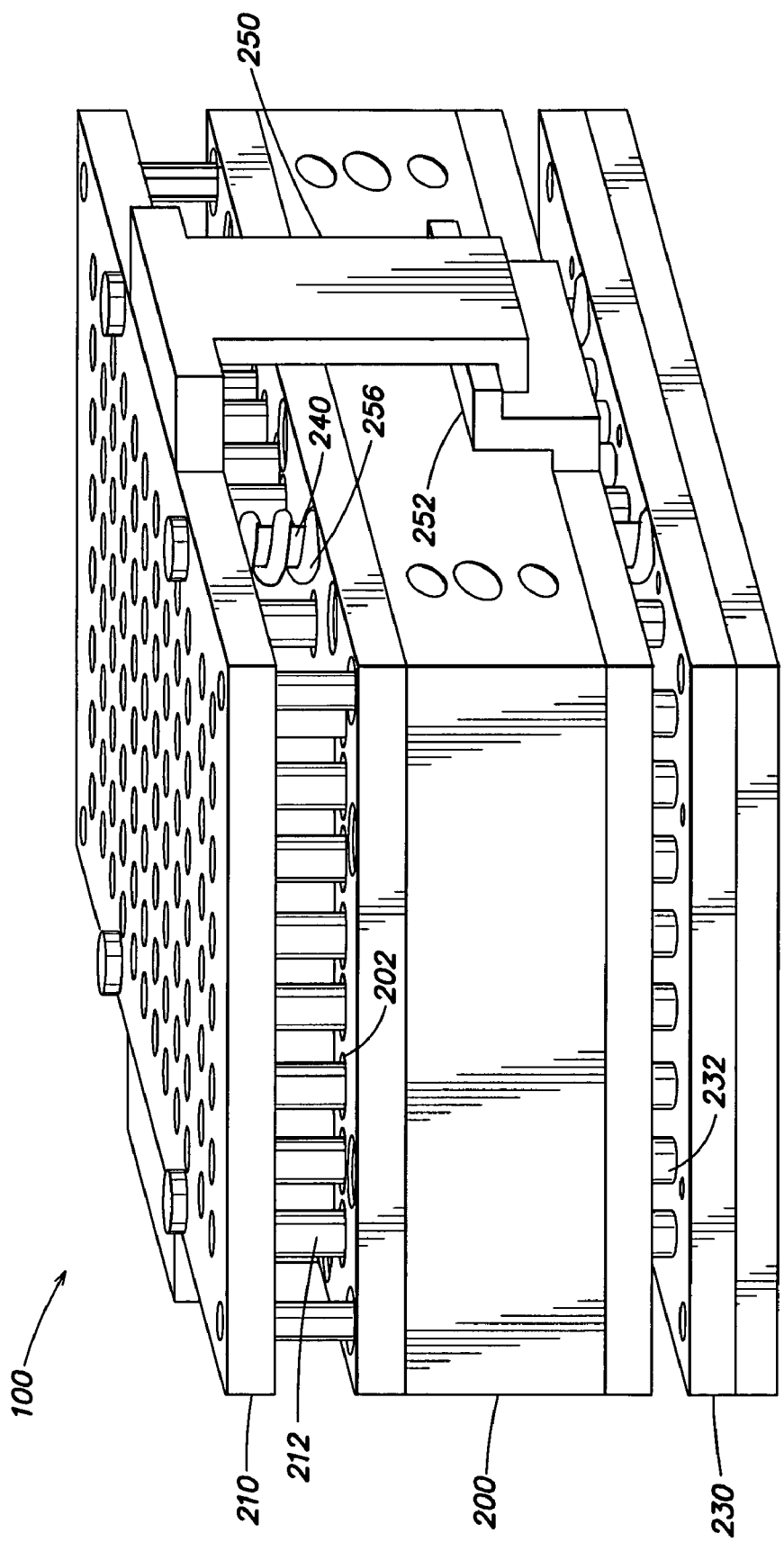
FIG. 3 illustrates a perspective view of the pipette module.
Figure 3B:
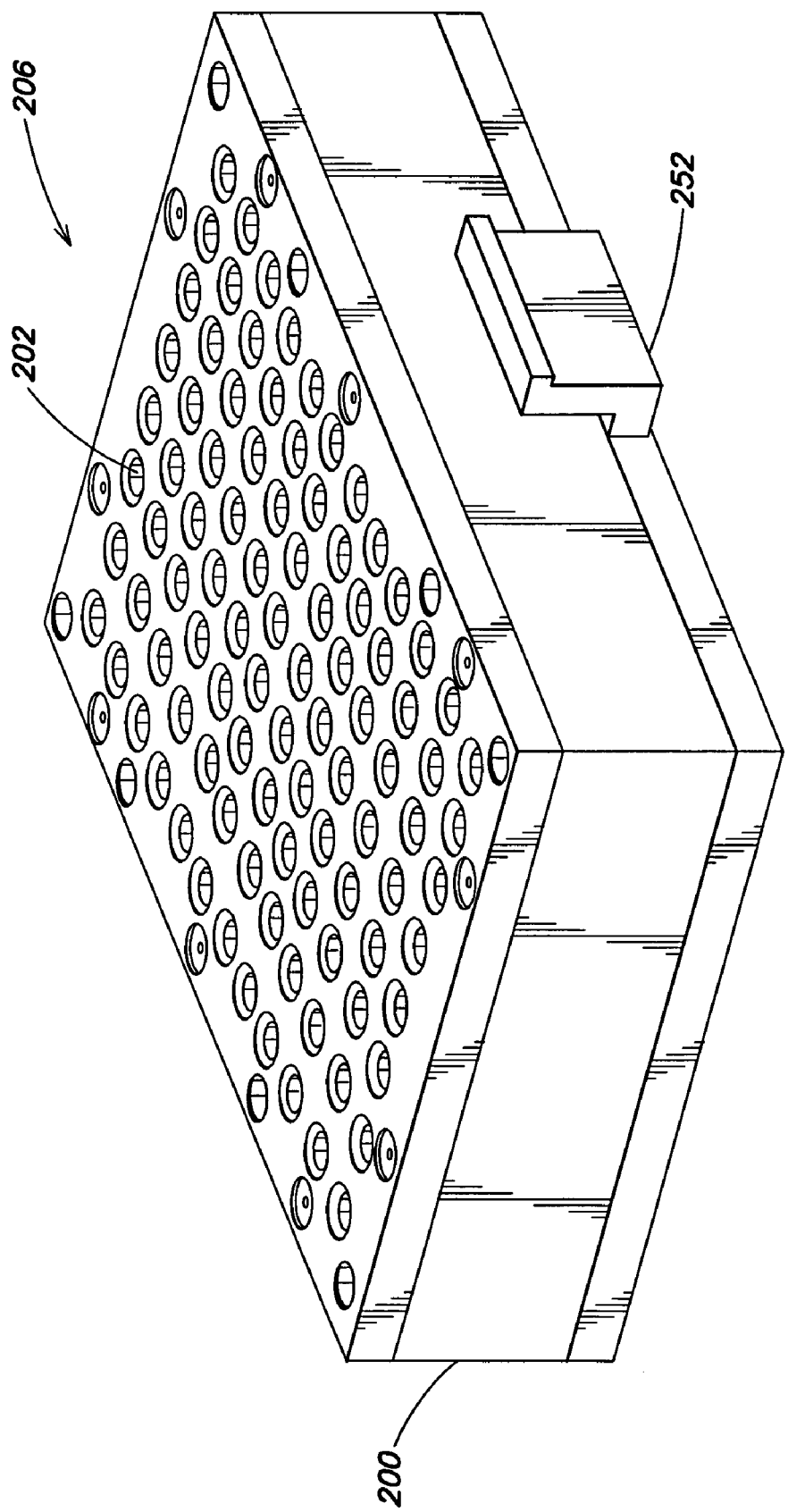

The embodiment of FIG. 3 illustrates the pipette module 100 of the present invention, which features a plurality of pipettes that are each similar to the above described pipette 10. FIGS. 3A–3D illustrate each subassembly in further detail. The pipette module 100 comprises a channel block 200 which has a plurality of parallel cylindrical passageways 202. As later described, the channel block 200 is similar to the above described channel 40, and the cylindrical passageway 202 is similar to the above mentioned internal chamber 80 of the pipette 10. As shown in FIG. 3B, each passageway 202 extends through the entire width of the channel block, and includes a counterbore 204 at each respective end of the passageway 202. The counterbore 204 is made to hold a compression seal or O-ring 238. The seal or O-ring 238 located at each end of the passageway 202 seals the internal chambers 280 (FIG. 4A) within each passageway 202 as the rods 212, acting as pistons, are slid over by the channel block, and also as the channel block 200 slides relative to the cylinders 232.

Located above the channel block 200 is the top assembly 205 as further shown in FIG. 3A. The top assembly 205 consists of top plate 210, which connects a plurality of rods 212, typically arranged in parallel, in a plurality of rows and columns. The rods 212 are sized, shaped, and aligned to pass into corresponding cylindrical passageways 202 from the top, in vertical movement relative to the top plate. In this embodiment, the top assembly also includes alignment posts 240 (FIG. 4A) to assist in aligning the top assembly 205 and thereby its rods with the cylindrical passageways. Further, the top assembly 205 is provided with a hanging ledge 250 to connect the assembly as described below.

Figure 3C:
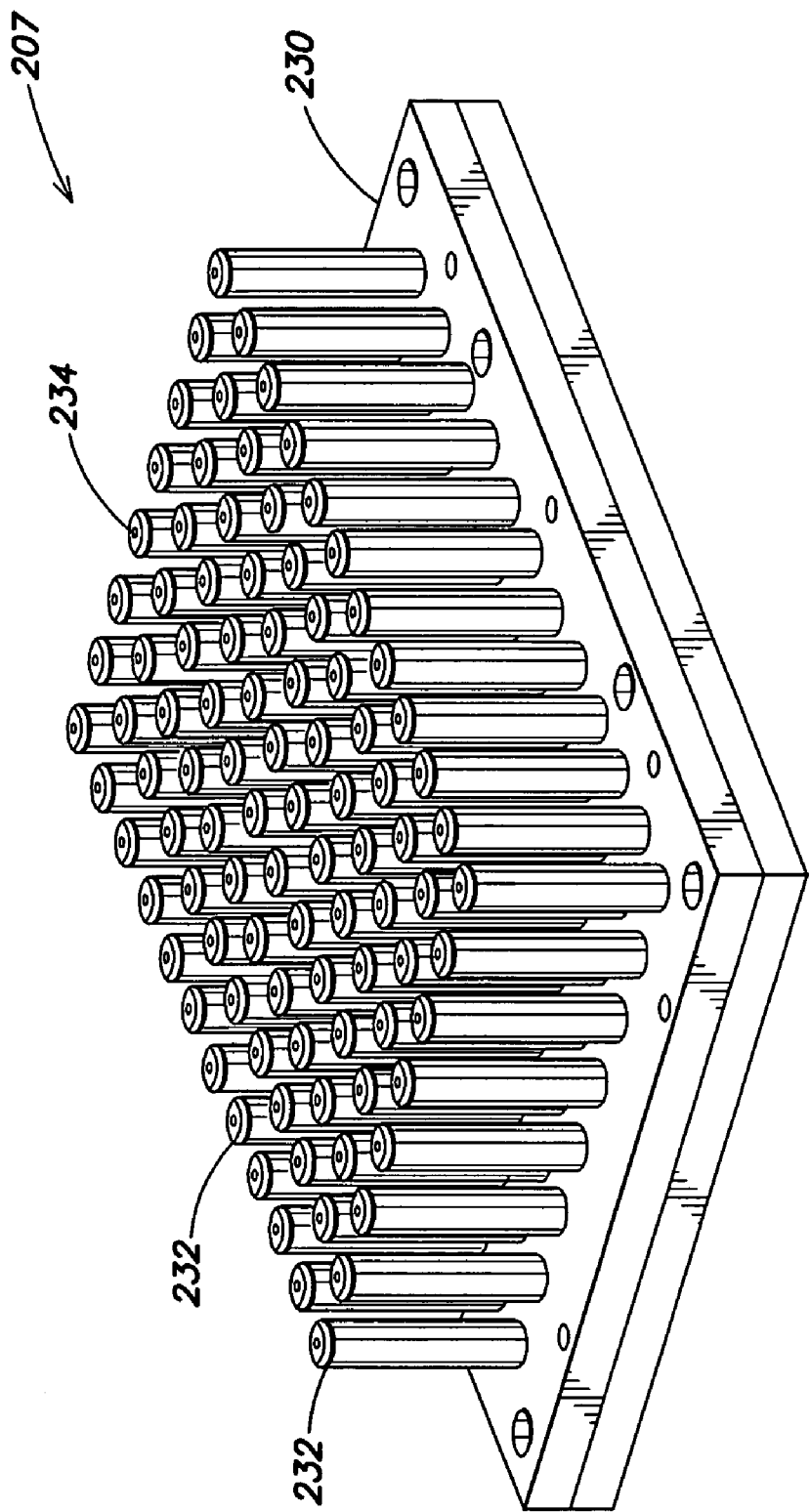

As shown in FIG. 3B, the middle assembly 206 consists of the channel block 200 with the plurality of cylindrical passageways 202. Each cylindrical passageway is provided with upper and lower seals or O-rings 238 that seal the internal portion of the passageway. The middle assembly 206 also includes a ledge gripper 252 which interlocks with the hanging ledge 250 as described in more detail below. Located below the channel block 200 is bottom plate 230, as shown in FIG. 3C, which connects a plurality of cylinders 232 with axially passages 234 extending therethrough. The bottom plate 230 is part of the bottom assembly 207. The cylinders 232 are sized, shaped, and aligned to pass upwardly into the corresponding cylindrical passageways 202 in the channel block 200.

Figure 3D:
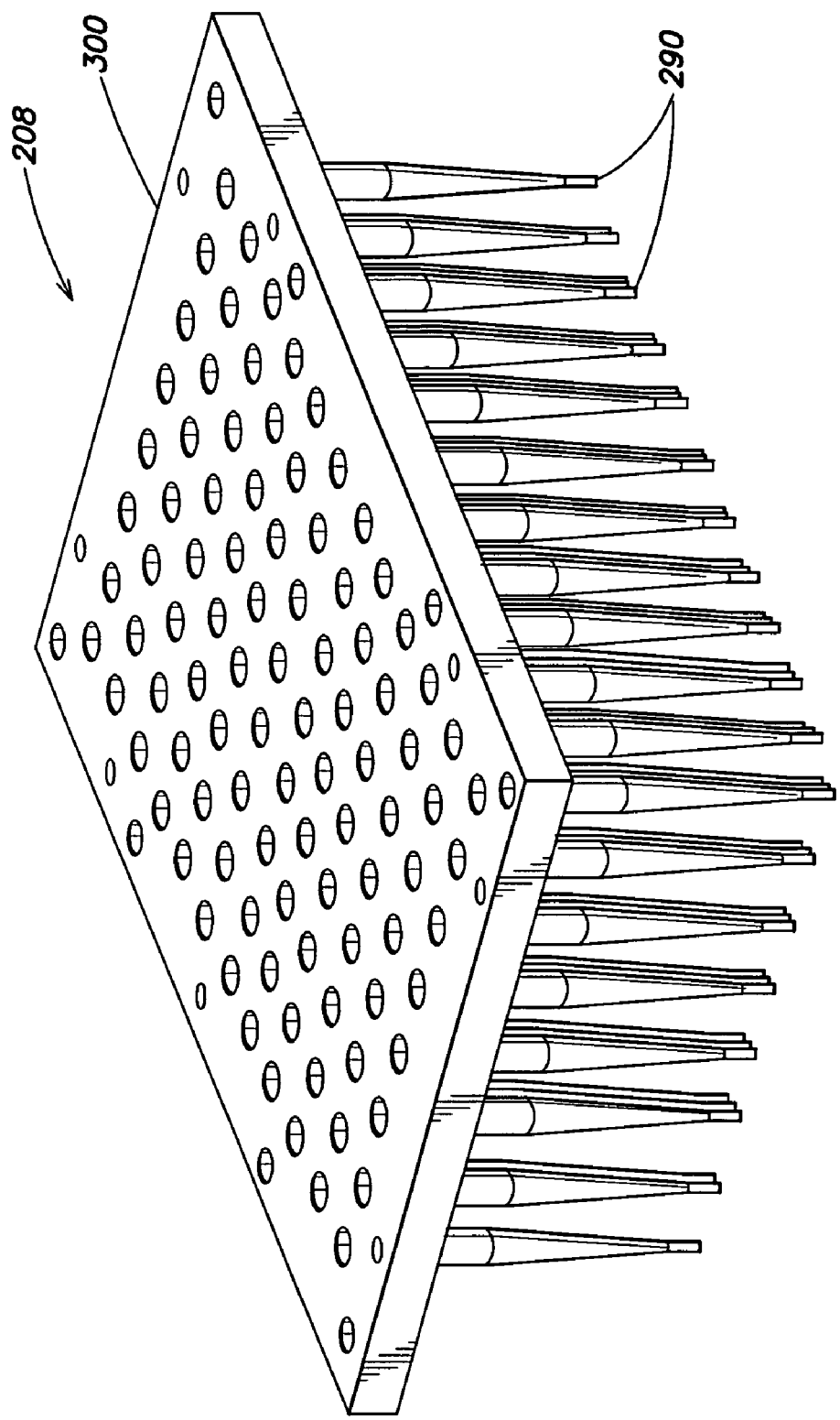

Below the bottom plate 230 is an interchangeable tip assembly 208 as shown in FIG. 3D. The tip assembly includes tips 290 that correspond to the axial passages 234 that extend through the plurality of cylinders 232. The tips 290 may be either the permanent kind, and made of a material such as steel, or alternatively, the tips may be disposable, typically made of plastic such as polycarbonate. In one embodiment, a rack 300 holds a plurality of tips 290 that are axially aligned with the passages 234 in the cylinders 232. The rack 300 may also be made of a disposable material, such as polycarbonate. A plurality of disposable tips 290 coupled to a disposable rack 300 may provide an easy way to replace multiple tips in a quick efficient manner. The tips may alternatively be individually threaded to the cylinders 232. The above described subassemblies may be stacked and aligned together, or alternatively, the subassemblies may be integrated together.

A typical air-filled pipette aspirates a sample by first placing the probe tip 290 into a fluid sample. By increasing the volume of the internal chamber 80, a sample volume is aspirated into the probe tip 290. With no change in density of the air within the system, the volume of the fluid sample equals the volume increase of the internal chamber 80. However, if the density of the air changes, the volume change in the chamber will not exactly equal the volume of the sample. For example, if the air within the chamber becomes less dense and expands during the aspiration process, the volume of the sample aspirated will equal the volume change minus the volume change of the air. Conversely, if the air is compressed, and becomes more dense during dispensing, then the volume dispensed will be less. A large air dead space also cushions blow-out force and a large blowout flow rate is needed to overcome this. The present invention looks to minimize the unnecessary air space, or dead space to help minimize the measurement error, while also providing both very fine resolution for aspiration and a very large flow rate to overcome the air cushion for dispensing when needed.

Figure 4A:
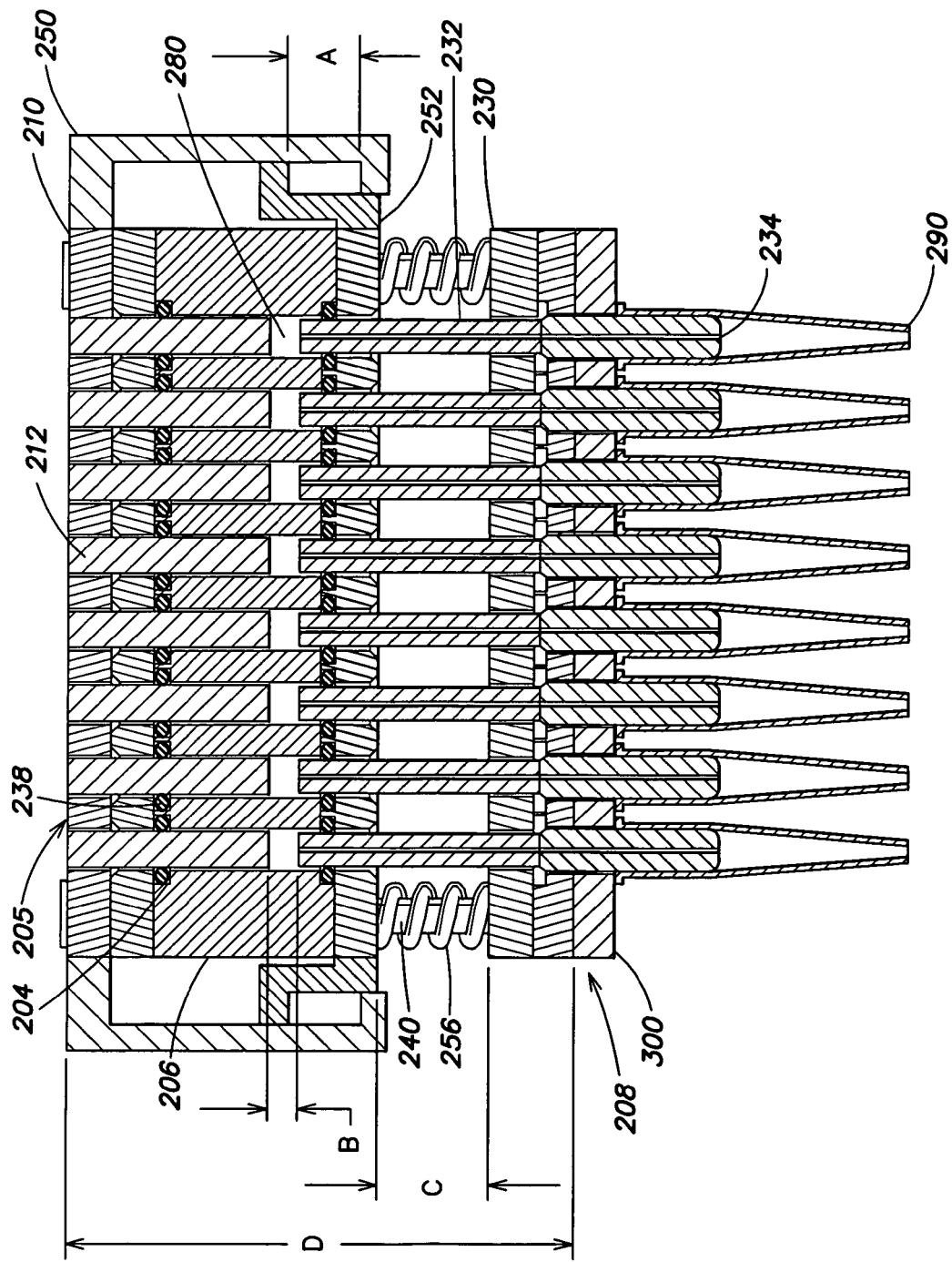

FIG. 4A shows a cross-sectional view of one embodiment of the present invention in the "Home position" or the top of the Differential Mode. The middle assembly 206 is at the top, positioned up against the bottom of the top plate 212. The helical springs 256 are in full extension holding the top assembly 205 up.

Figure 4B:
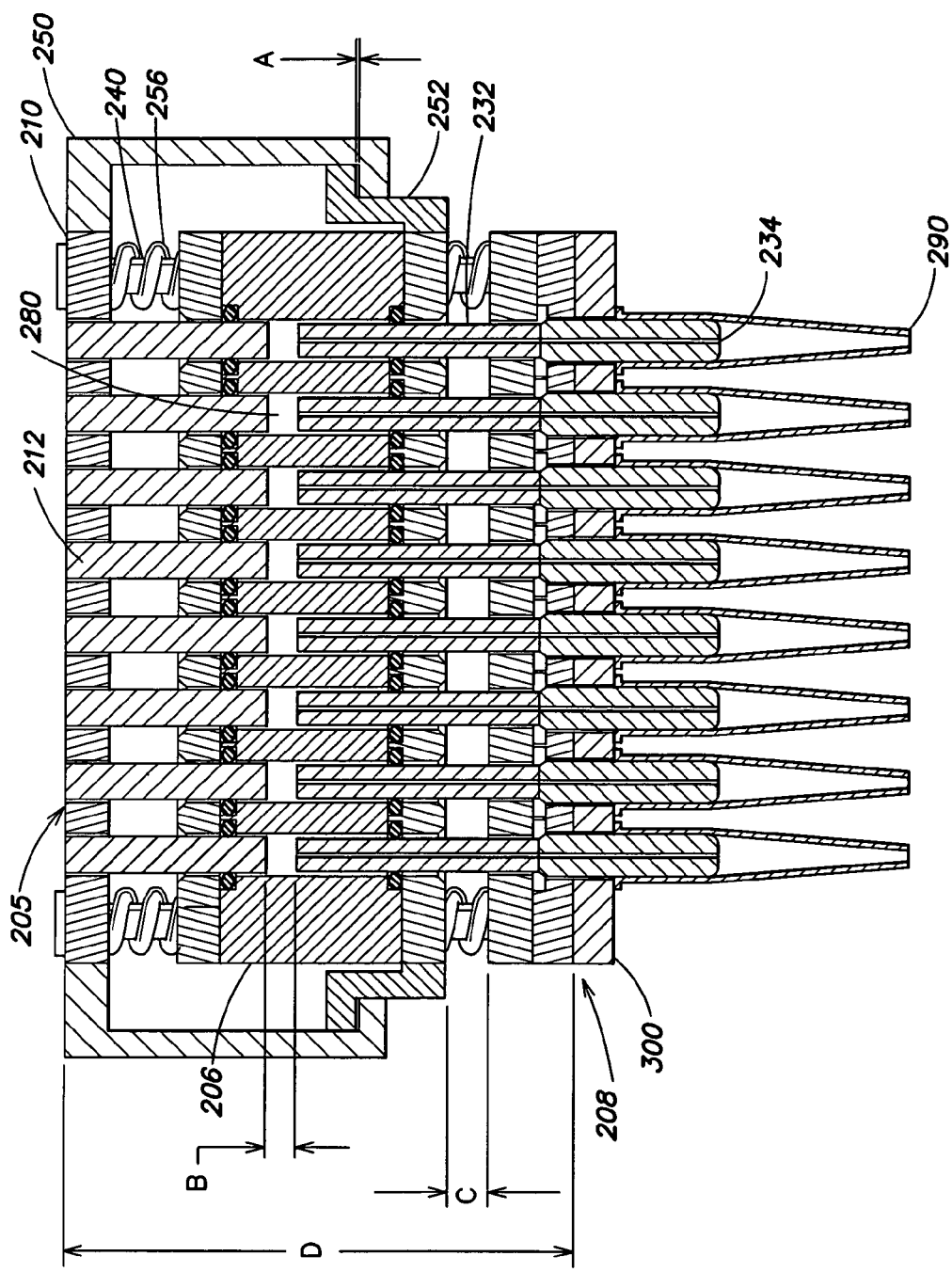

In FIG. 4B the middle assembly 206 moves down to a position determined by the volume of the fluid sample one intends to aspirate. This illustrates the start of the differential aspiration. The middle assembly 206 is positioned such that at the end of aspiration, the middle assembly will be positioned close to the transition level between Differential and Bulk Mode. FIG. 4B shows the start position for aspirating a 100 nanoliter sample in Differential Mode, which corresponds to positioning the middle assembly such that the hanging ledge 250 is spaced from the ledge gripper 252 by 0.007" as illustrated as dimension A.

Figure 4C:
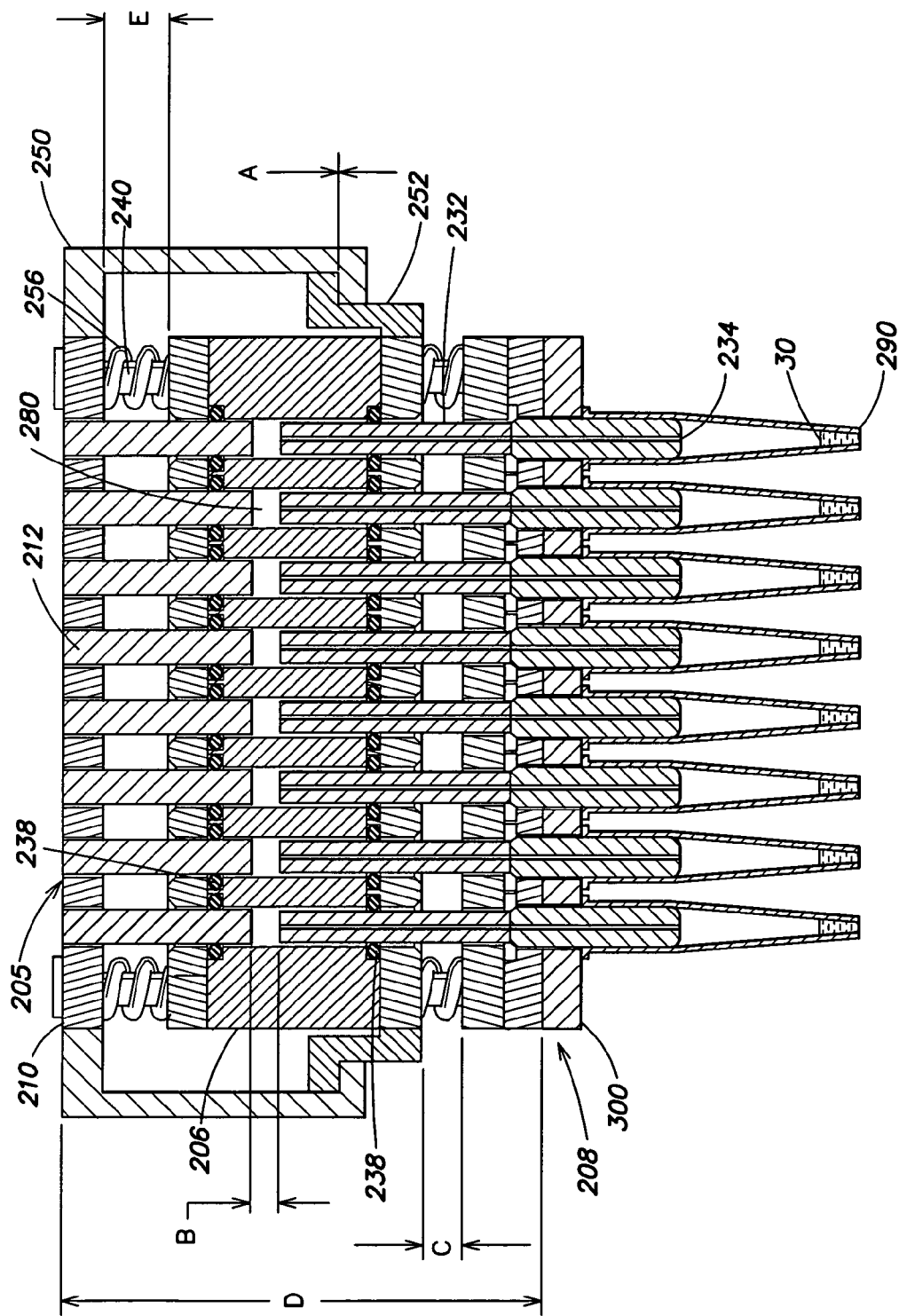

FIG. 4C illustrates the end of the 100 nanoliter aspiration. The middle assembly 206 moves down from the position in FIG. 4B, aspirating the sample, while decreasing the space between the hanging ledge 250 and the ledge gripper 252 until they are adjacent. This contact marks the transition level from the Differential to Bulk Mode of operation, to be discussed in the dispensing section below. The top assembly 205 remains stationary while the middle assembly 206 moves down, therefore the seals, such as O-rings 238, in the middle assembly 206 sweep down over both the top rods 212 and the bottom cylinders 232. During this process, the channel envelops more of the bottom cylinders while releasing the top rods. Since the rods 212 have a slightly greater diameter in comparison to the cylinders 232, the movement of the middle assembly 206 creates a space or vacuum which causes the differential aspiration of the fluid sample as described above. This particular example provides an extremely fine resolution, such that the 100 nanoliter sample aspirated in Differential Mode could only be achieved by a conventional single piston pipette whose diameter was an impractically small 0.033 inches (See FIG. 5), but which is achieved by the present invention with the very practical sizes of 0.187 inch and 0.184 inch diameters (See FIG. 5).

The top and middle assemblies of the present invention may move either manually or automatically. In one embodiment, movement of the top assembly 205 is controlled by a spring assembly. In one embodiment, the middle assembly is controlled by a motor, typically a stepper or DC motor. The present invention provides a "blow-off" through the use of Bulk Mode to adequately expel a sample. Since the pipette may be motor driven, the "blow-off" velocity can easily be controlled to maintain the integrity of the sample.

FIG. 4D illustrates the end of the dispensing of the fluid sample, where the sample was dispensed in Bulk Mode. Just prior to the dispensing of the sample, the top assembly 205 becomes linked to the middle assembly 206 by the ledge gripper 252 and the hanging ledge 250 coming into contact. This contact marks the transition from Differential to Bulk Mode operation. This linkage permits the top assembly 205 to move down with the middle assembly 206 as the middle assembly slides further down. As previously described, movement of the rods 212 and the channel block 200 together places the stationary cylinders 232 farther into the channels 280. However, since the rods 212 are anchored to the channel block 200 and move down with the channel block 200, the rods 212 maintain their position within the channels 280. With this action, the only volume change in the internal chamber is a decrease, caused by the entry of the stationary cylinder 232 into the internal chamber 280 as the channel block 200 sweeps down over the cylinder. The high flow rate produced blows the sample completely out of the probe tip, providing a touchless transfer without any "hanging drop". This accurate touchless transfer of the fluid sample is easily provided with a pipette that meters in two modes of resolution. The smaller Differential Mode enables the aspiration of a small or minute sample volume, while the larger Bulk Mode enables the complete dispensing of the fluid sample out of the probe tip. As previously described, the tip assembly includes a plurality of tips 290 that are axially aligned with the passages 234 in the cylinders 232. In one embodiment of the rack 300 holding the tips, the rack and tips are disposable for ease of use.

The above-described pipette module 100 allows for the simultaneous metering of multiple samples at once because of the array of individual pipetting chambers that will each aspirate and dispense a fluid sample. Since all of the pipetting chambers are linked together through the pipetting module, the present invention enables all of the samples to be simultaneously metered through movement of the top assembly 205 and channel block 200. With the use of the Differential and Bulk Modes, the present invention is able to overcome the cushioning effects of air within the pipetting system, both at the aspiration and delivery ends, while also enormously increasing the operating volume range of an air-filled pipetting system. By switching between two resolutions, the present invention allows one to maximize the variety of sample sizes that are accurately metered.

FIG. 5 illustrates a table comparing one embodiment of the present invention with conventional pipette systems. A tip velocity of 1.5 meter/second may be considered as the minimum tip velocity required for a small drop to escape the surface tension of the tip for a clear non-viscous sample. Standard commercial pipettes are therefore usually between 0.062" and 0.125" in diameter to assure a sufficient tip velocity to blow-off the sample, as shown in FIG. 5. However, as illustrated, with a conventional air pipette of this size, there is a sacrifice in resolution. The hypothetical conventional pipette at the top of FIG. 5 illustrates a pipette that would provide a resolution of 14 microliters/inch, but as shown, this hypothetical pipette would not be capable of providing a sufficient tip velocity to reach the minimum tip velocity. Further, such a hypothetical pipette would be difficult to seal due to the small 0.033" diameter. The bottom column of FIG. 5 shows that the present invention provides a Differential Mode capable of metering small samples, with a fine resolution of only 14 microliters/inch, corresponding to a robust 1.8 millimeters excursion per microliter, while also providing a Bulk Mode with a huge flow resolution capacity of up to 454 microliters per inch that provides the capability to achieve a tip velocity greater than 1.5 meter/second even with non-clear and viscous samples.

Figure 6:
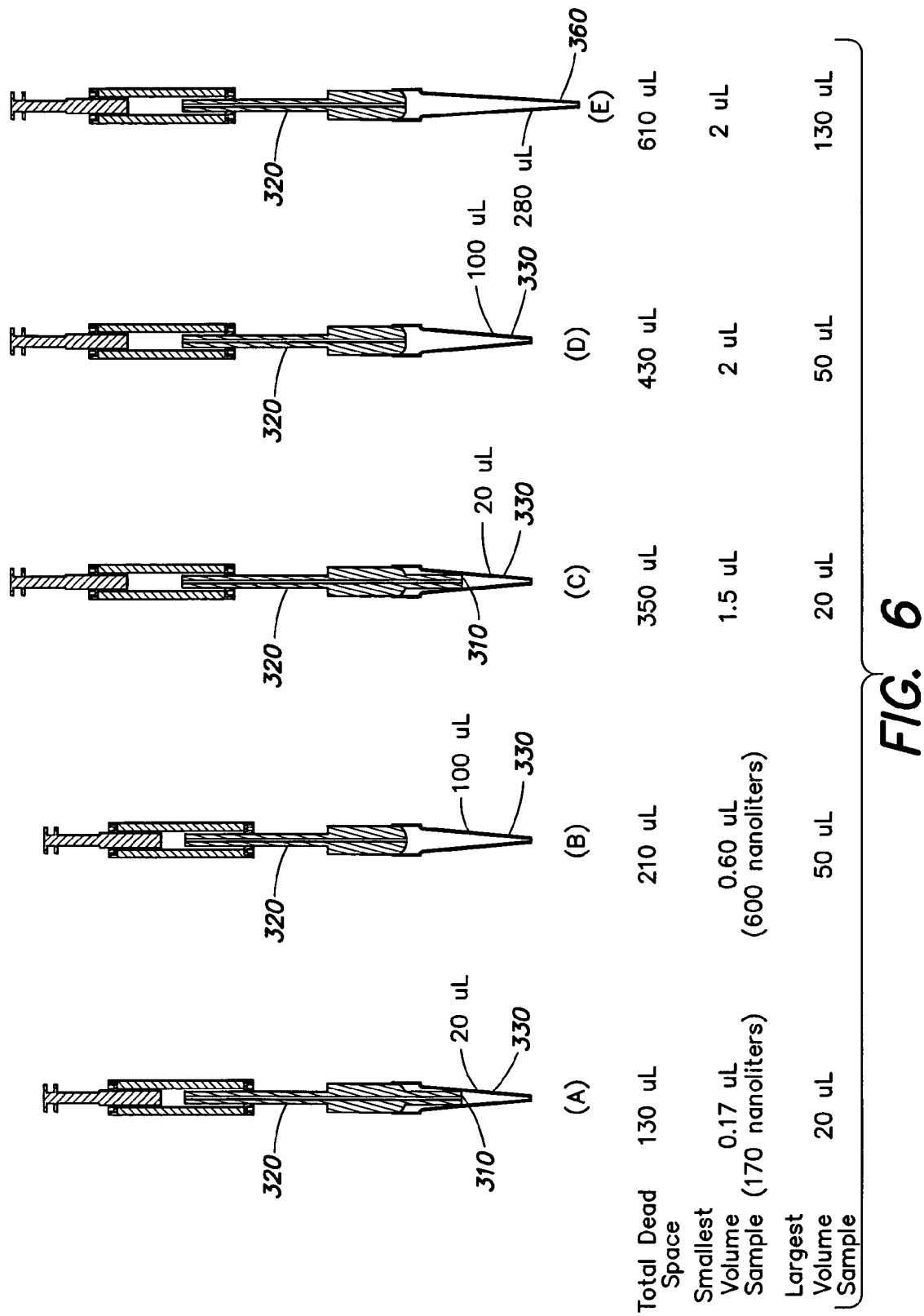
FIG. 6 illustrate pipettes with standard commercial tips with and without the extension mandrel.

While the above described dual mode helps to minimize the measurement volume range limitations and error associated with large areas of dead space within the pipette system, the present invention also looks to minimize the unnecessary dead space in the tips even further with the use of an extension mandrel, which may be removable. FIGS. 6A–6E illustrate two standard commercial tips held by the present invention with a standard mandrel shaped end, and with a mandrel modification which includes an extension space-filling mandrel. FIGS. 6A–6D, shows that a Labcon 50 tip 330 has an internal volume of approximately 100 microliters when attached to a conventional pipette 320 mandrel. However, when an extension mandrel 310 is used, either as a permanent part of the mandrel or as a removable mandrel that attaches to the pipette 320, the internal "dead space" volume within the tip 330 is reduced to only 20 microliters. FIG. 6E shows a larger tip, the Labcon 200 or Costar 200 tip 360, which when held by a standard mandrel has a large internal volume of approximately 280 microliters. The series of five pipettes therefore shows total dead air space volumes that decrease progressively from right to left from a high of 610 microliters to a low of 130 microliters. FIG. 6 shows that the reduction in dead space within the tip reduces the interference from air compressibility, permitting the system to aspirate and blastoff touchless even more minute samples.

The two larger air space systems shown in FIGS. 6D and 6E permit the present invention to pipette a sample as small as 2 microliters, and in FIG. 6E, because the tip is so large, a sample as large as 130 microliters may be conveniently handled. From FIGS. 6C to 6B to 6A, reductions in air space from 350 microliters to 210 microliters, and then down to 130 microliters makes it possible to aspirate a sample as small as 1.5 microliters, then 0.60 microliters, and then finally down to 170 nanoliters with the extension filler mandrel of FIG. 6A.

Figure 7B:
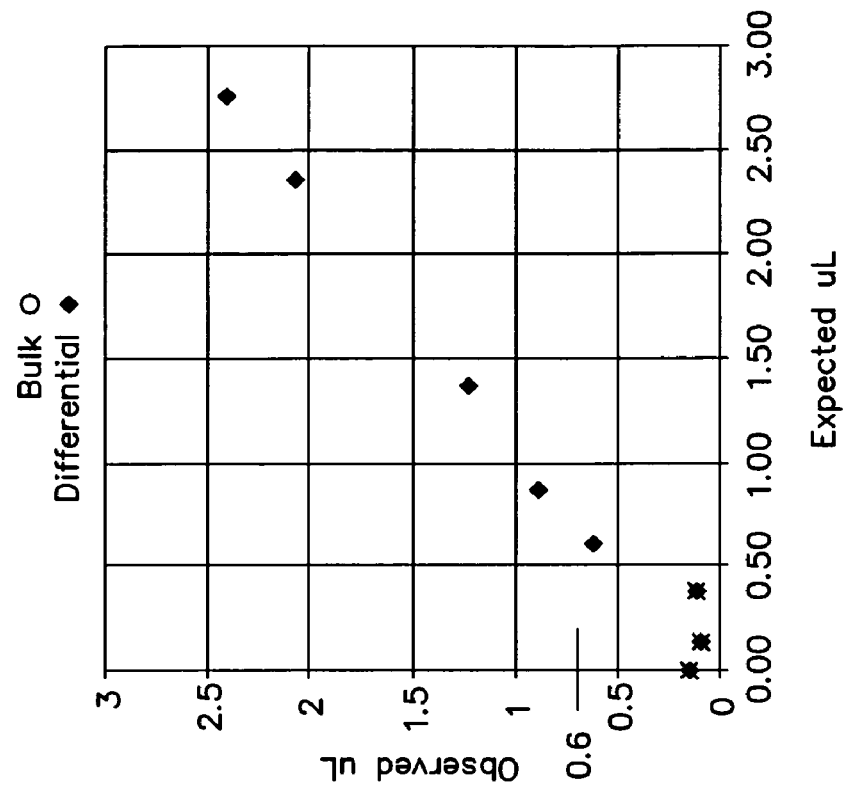
FIGS. 7A–7B illustrates data for wide range aspiration in both Differential and Bulk Mode and contact-free Blastoff in Bulk Mode for one embodiment of the present invention that has a relatively large amount of internal dead space.
Figure 7A:
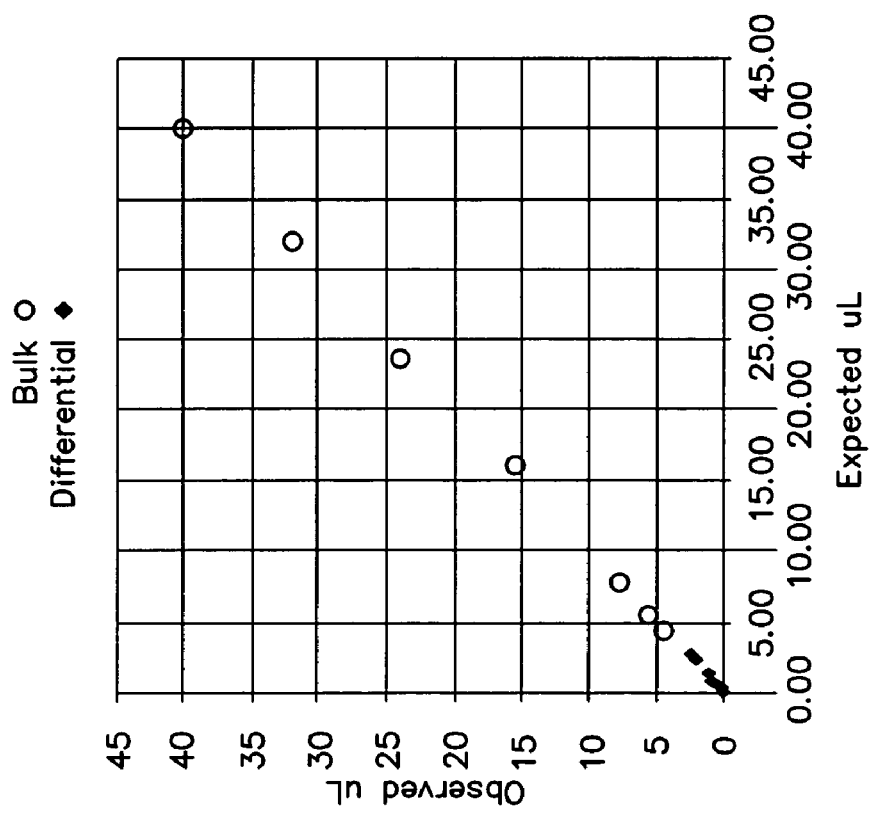

FIGS. 7A–7B show data illustrating the linear (accurate) operating range based on measuring the pipette samples that are dispensed from the pipette. This particular embodiment has a rod diameter of 0.187 inches and a cylinder diameter of 0.184 inches. As FIG. 5 shows, this has a Differential mode with a fine resolution that would be equivalent to a conventional pipette having a tiny diameter of 0.033 inches, which is known to be impractical both because it is difficult to seal and also because it would not be able to blow off the sample.

The linear relationship in FIG. 7 shows how low the pipette can accurately go. The open circle data points correspond to Bulk mode of the present invention, which is comparable to the results one would expect to achieve with a typical large air pipette. The solid diamond data points correspond to Differential Mode. As shown in FIG. 7A, Differential Mode enables the present invention to be able to accurately meter sample volumes below 3 microliters, which would not be possible with Bulk Mode alone, or with a conventional air pipette.

FIG. 7B is a magnified view of the smaller sample volumes in FIG. 7A, focusing only on the range in Differential Mode. As illustrated, in this embodiment, the pipette is able to provide a linear and accurate relationship down to sample volumes of approximately 600 nanoliters. In this embodiment, one cannot consistently and accurately pipette samples smaller than 600 nanoliters.

Figure 8:
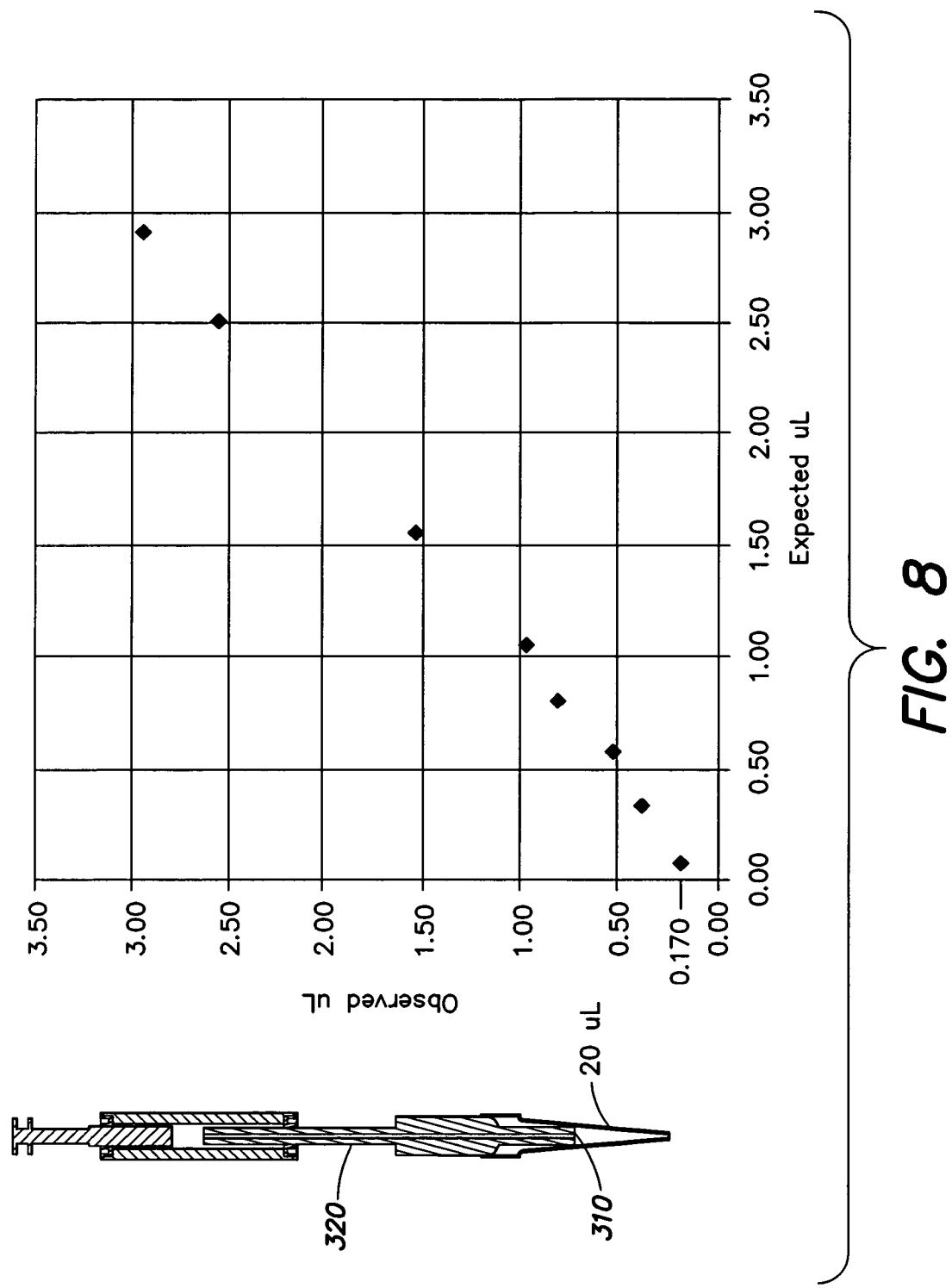
FIG. 8. illustrates data for minute volume aspiration in Differential Mode and contact-free Blastoff in Bulk Mode for one embodiment of the present invention with the extension filler mandrel and a relatively small amount of internal dead space.

However, as previously described, an extension mandrel provided on the pipette can further reduce the interference caused by the compressible air within the system. The embodiment in FIG. 8 is identical to FIG. 7, except that an extension mandrel or filler mandrel 310 has been added which reduces the internal dead space from 210 microliters (as in FIG. 7) to 130 microliters. With this reduction in internal dead space, this embodiment of the present invention is capable of providing a linear relationship, and thereby accurately pipetting down to about 170 nanoliters, as shown in FIG. 8.

Figure 9A:
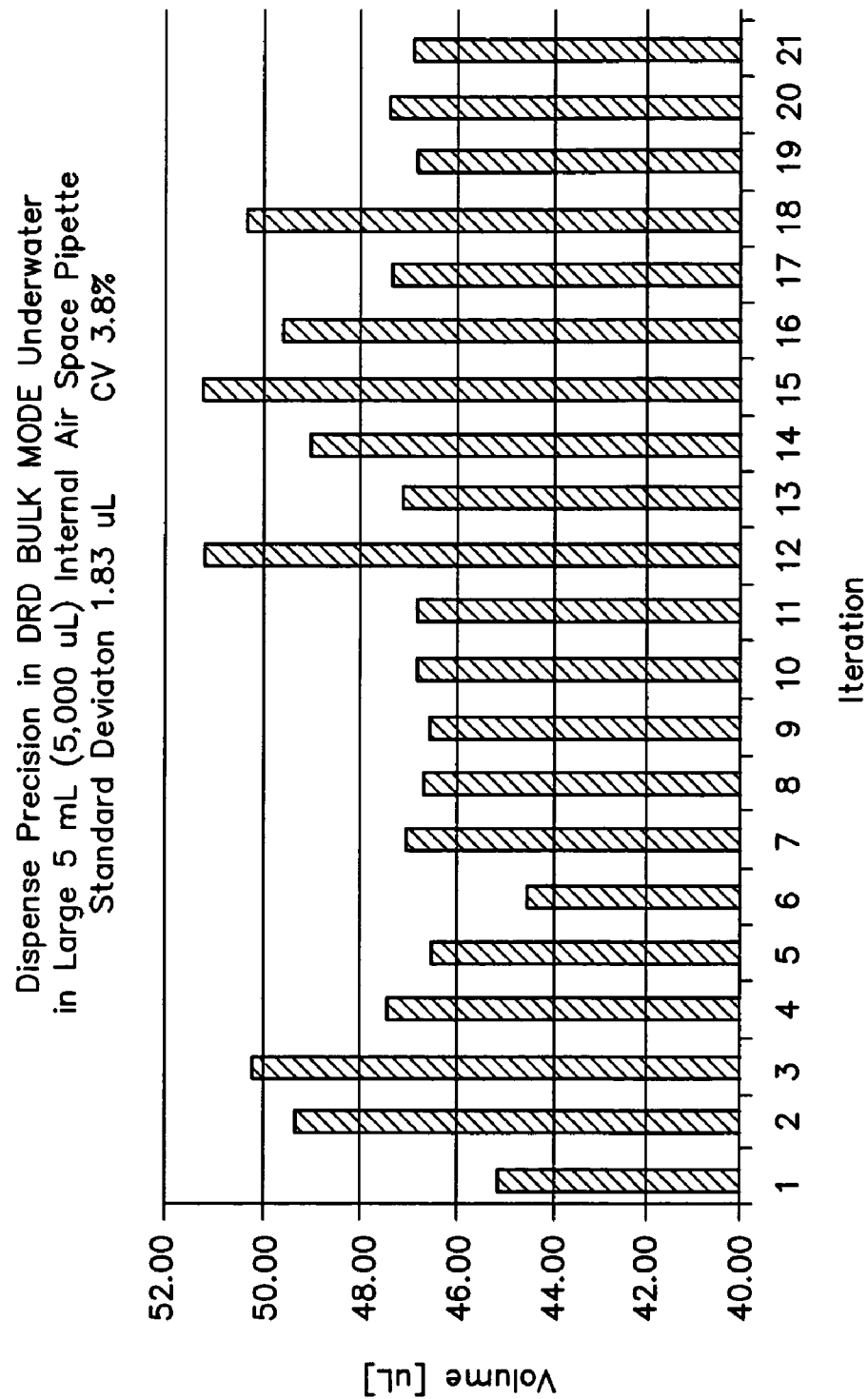
FIGS. 9A–9B illustrate the dispensing precision in Differential Mode compared to Bulk Mode in a large internal air space pipette.
Figure 9B:
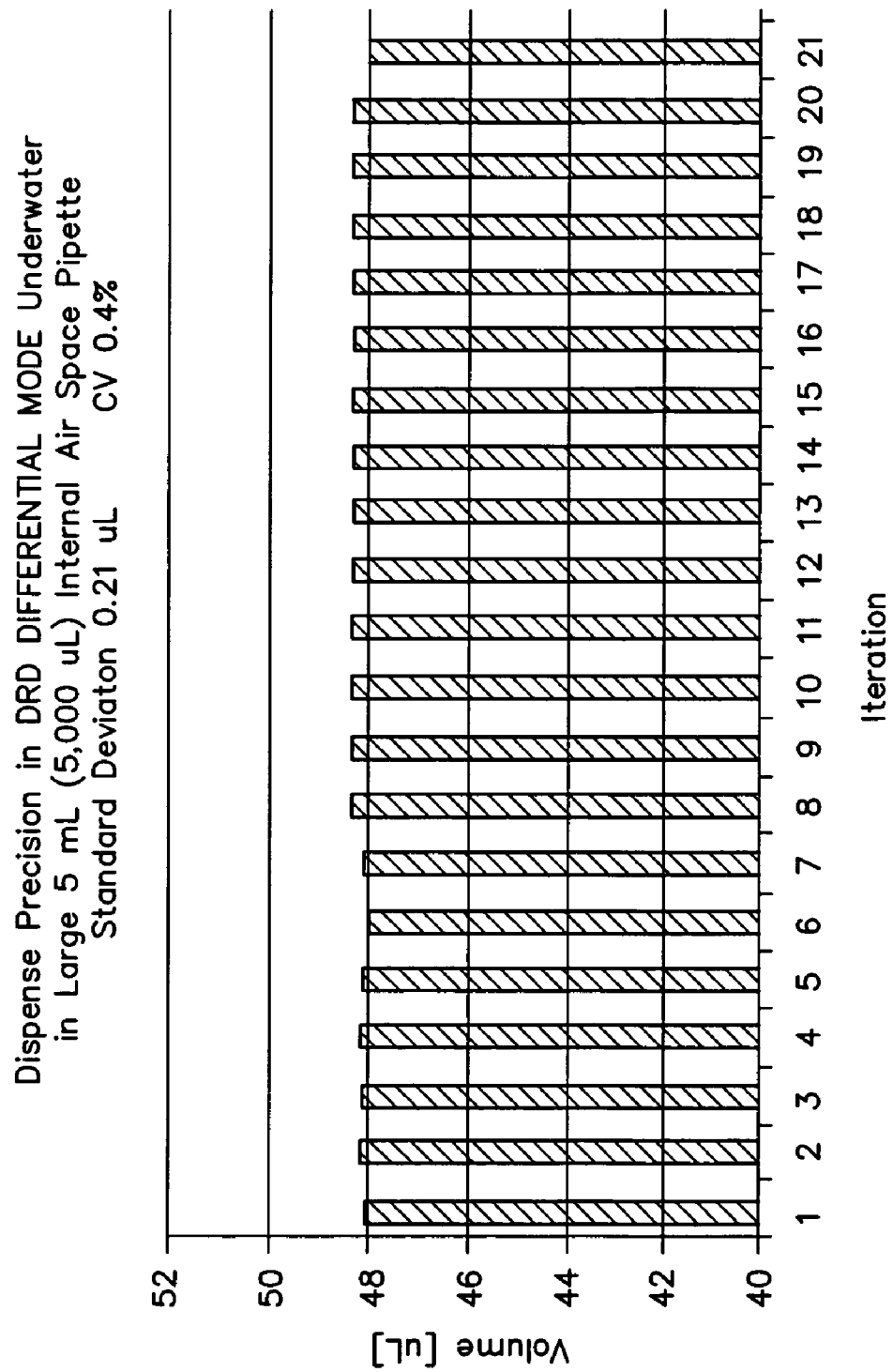

FIG. 9 illustrates the comparison of the dispensing precision in both Differential and Bulk Mode. As shown in the bar graphs, the precision is increased with Differential Mode. The data in FIG. 9 reflect dispensing in the two different modes of the present invention with a relatively large, 5 milliliter (500 microliter) internal air space within the pipette. For simplicity, the data was collected with the pipette tip under water to minimize the effects of dispensing in air and the occurrence of hanging drops on the pipette tip. As shown, with Bulk Mode, a standard deviation of 1.83 microliters was achieved in 21 iterations. Since the mean sample volume was 48 microliters, the coefficient of variation (CV) was 3.8%. Similarly, in Differential Mode, the standard deviation in 21 iterations was only 0.21 microliters for a 48 microliter sample, thus producing a coefficient of variation (CV) of only 0.4%.

FIG. 10 further illustrates the extension mandrel filler 410, which may be removably secured to, or part of the main body portion of the pipette 400. As shown in FIG. 10.1, the extension mandrel 410 has a cross-sectional area that is less than the cross-sectional area of the main body portion of the pipette 400. When a disposable pipette tip is secured to the end of the pipette, this reduction in cross-sectional area enables the extension mandrel 410 to fill a volume within the pipette tip 430 that the main body portion of the pipette 400 alone would not be capable of filling. In other words, the extension mandrel 410 functions to reduce the volume of air that occupies the pipette tip 430. In the embodiment of FIG. 10, the extension mandrel 410 reduces the volume within the pipette tip from 280 microliters to only 20 microliters. As explained above, in an air-filled pipette system, a reduction in the air within the pipette and pipette tip decreases the measurement error associated with density changes in the air. In one embodiment that features an extension mandrel 410, the main body portion of the pipette 400 transitions to the extension mandrel in a step arrangement, however, other configurations, such as a sloped transition, are contemplated.

One advantage of the extension mandrel is that when a disposable pipette tip 430 is secured to the end of the pipette, the disposable pipette tip contacts both the main body portion of the pipette 400, and the extension mandrel. This helps to stabilize the disposable pipette tip with respect to the pipette. As shown in FIG. 10.2, when the disposable pipette tip 430 is secured to the pipette and contacts the pipette at least at two distinct locations on the pipette, axial alignment and stability is further achieved. Axial alignment becomes even more critical when there is an array of multiple pipettes and removable pipette tips, which typically are arranged in groups of either 96 or 384. A slight tilt of the pipette tip 430 with respect to the pipette 440 may prevent the alignment of adjacent pipettes and pipette tips. Further, because the extension mandrel enables the pipette to rest farther inside the pipette tip, about 1.25 inches into the tip as shown in FIG. 10.2, there is increased stability in comparison to a pipette 440 without an extension mandrel secured to a disposable pipette tip, shown in FIG. 10.2 as only extending into the tip 0.25 inches.

Additionally, FIG. 10.3 illustrates the versatility of the extension mandrel. First, if the extension mandrel is removable, the main body of the pipette may be used simply in combination with a pipette tip. Further, the extension mandrel 410 may be secured to the main body of the pipette 400 to limit the air volume, and finally, in some applications, the extension mandrel 410 itself may be used as a fixed tip when secured to the main body portion of the pipette.

Each pipette may pick up one or more portions of reagents or air buffers, as well as samples, and mix them by means of the touchless blastoff process. This is desirable in a variety of applications. For example, the mixing may be for diluting a sample with a reagent, such as in a wide variety of reactions used in analytical chemistry. Typically the reagent is aspirated into the tip first as shown in FIG. 11.1. Although aspiration is possible in either Bulk or Differential Mode, in this particular embodiment illustrated, a small 1 microliter portion of the reagent is aspirated in Differential Mode. To prevent contaminating a subsequent sample, one may then aspirate a quantity of air to act as a buffer between the first sample and the soon to be aspirated sample. As shown in FIG. 11.2, this particular air buffer is 0.5 microliters. The sample is then aspirated through the tip, as illustrated in FIG. 11.3, as a 0.2 microliter sample. Although the two liquids remain separated by the air buffer within the pipette, as shown in FIG. 11.4, when the two samples are ejected from the pipette tip (typically in Bulk Mode), the samples mix as they drop onto a surface. The variation of the speed in which the present invention can blastoff or dispense the samples enables an appropriate speed to be selected for the mixing of the samples. The blastoff speed can be precisely selected to achieve the desired degree of mixing when the larger reagent drop lands on top of the smaller sample at the desired target location. Another application for this is in Maldi Toff analysis, in which a matrix liquid "carries" a sample to the receiving site, where a laser converts the sample into an ion stream for introduction into a mass spectrometer for quantitative analysis.

Another way that multiple samples can be mixed in the present invention takes advantage of the tip geometry. In particular, this method may be used where the diameter of the tip changes, typically in the tapered disposable plastic tips commonly used. As shown in FIGS. 12.1–12.3, a first 1 microliter reagent 510 is aspirated through the tip 500, followed by a 0.5 microliter air buffer 520, followed by a smaller second 0.2 microliter sample 530. However, unlike the embodiment of FIG. 11, where the sample mixing occurs outside of the pipette, the embodiment of FIG. 12 illustrates sample mixing occurring within the pipette. As shown in FIG. 12.4 an additional second aspiration of air 540 pulls both the liquid samples farther up into the tip up to where, due to the larger diameter, the smaller sample becomes membranous. As shown in FIG. 12.5, further aspiration of air moves the samples to a location with a larger diameter, which will eventually cause the continuity of the smaller sample to break, thereby merging with the larger sample or reagent. To further completely mix the two samples, as shown in FIG. 12.6, the pipette can then oscillate the mixture up and down either smoothly in Differential Mode, or vigorously in Bulk Mode. Prior to the ejection of the mixed sample, the mixture 550 may be moved down closer to the pipette tip, as illustrated in FIG. 12.7. Finally, as shown in FIG. 12.8, the mixture 550 is dispensed from the pipette as a single homogeneous drop. And as described above, the blastoff speed of the drop may be precisely controlled for the particular mixture. A valve (not shown) provides further flexibility for such within-tip manipulations.

The above described method for mixing multiple samples together within a pipette provides numerous benefits. The dual modes of the above described pipette system advantageously provides the ability to precisely control the movement and mixing of the samples, while also providing a sufficient speed to completely blastoff the mixture. This enables a conventional disposable plastic pipette tip to become in effect a mixing chamber, delivering completed reaction chemistries to an analytical device.

Therefore, the present invention provides a method and apparatus to overcome the problems with the prior art that have limited the use of air-filled pipette systems. The dual resolution aspect of the present invention enables a wide range of samples to be accurately aspirated and cleanly dispensed from the pipette. Further, the extension mandrel filler helps to further reduce the internal dead space within the pipette, to lower even further the tiny size limit that can be pipetted.

In one embodiment, the above described pipette module is incorporated into a larger automated system to facilitate the physical movement of the pipettes, to transport microplates and tips to and from the pipettes, and to further analyze results produced from the fluid sample metered from the pipettes. In one embodiment, this auxiliary system combined with a pipette module creates a complete end product for testing a variety of fluid samples.

Figure 13A:
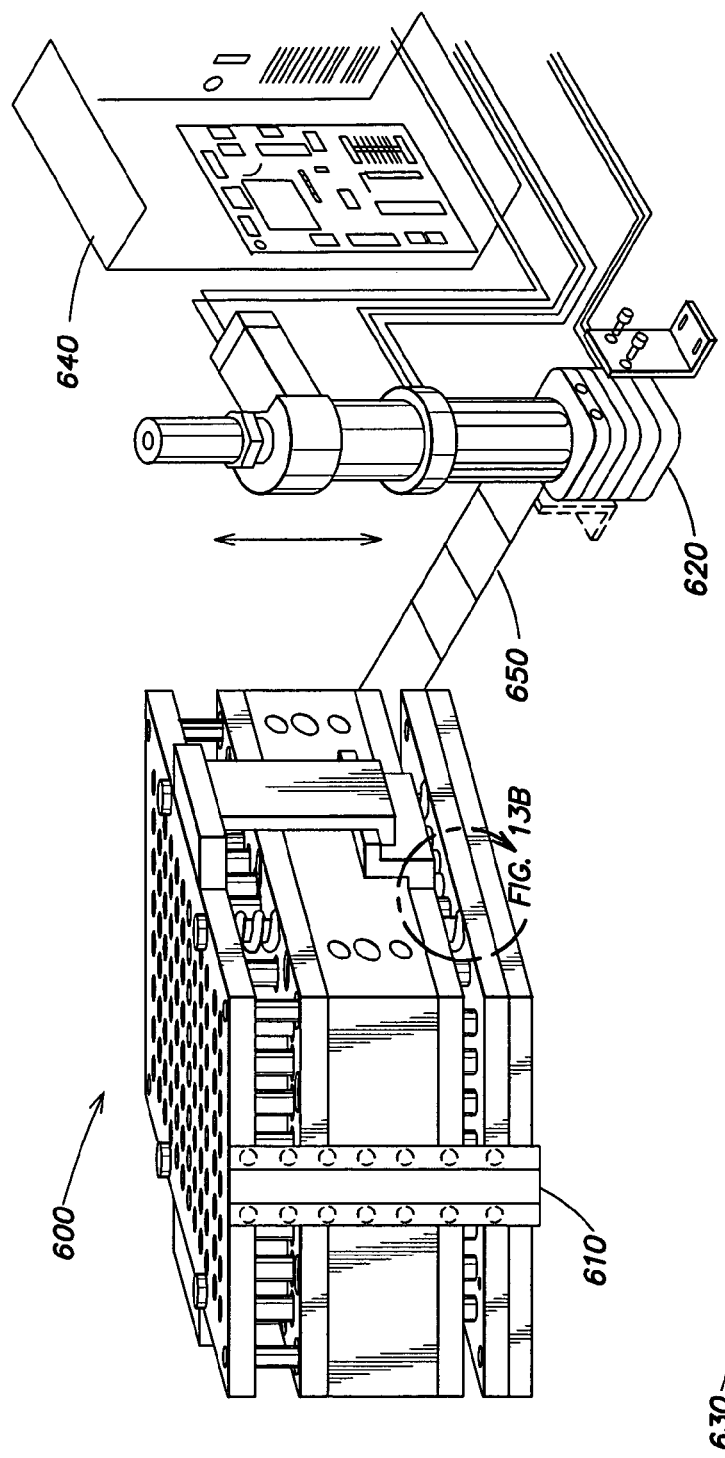
FIGS. 13A–13B illustrate a working module to help facilitate the placement and movement of the pipette.
Figure 13B:
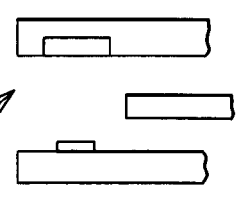

One example of a working module 600 to help facilitate the placement and movement of the pipette is shown in FIG. 13. The working module 600 includes alignment bearings 610, such as linear roller bearings, to precisely position the pipette module and permit the smooth axial movement of the channel block, rod plate, or cylinder plate of the pipette module. The working module also includes a motor 620 communicating with the pipette module to initiate movement of the channel block, rod plate, or cylinder plate of the pipette module. The working module also includes a position sensor 630 to sense the location of at least one of the channel block, rod plate, or cylinder plate. In one embodiment, the working module further includes electronic controls 640 and a communication port and linkage 650 in connection with the alignment bearings, motor, and position sensor, to control the movement of at least one of the channel block, rod plate, or cylinder plate. In one embodiment, the motor controls the vertical movement of the channel block relative to the cylinders.

Typically, fluid samples are aspirated from and dispensed into microplates. The working module may be incorporated into a system which conveys microplates to and from the pipettes, depending on whether the microplate is empty or contains a volume of a fluid sample or reagent. Alternatively, rather than microplates, the pipettes may dispense fluid samples onto flat plates or slides, which are typically glass, or into test tubes.

Further, as discussed above, the pipettes may include disposable tips. The working module may include conveyors that transfer new disposable tip packs to the pipette, and a waste catch to dispose of the used disposable tips. Also, in the event that the tips are reusable, the working module may include a wash basin to clean the tips in between uses. One conventional form of tip cleaning involves ultrasonic pulses.

Once the fluid sample is dispensed from the pipette into a microplate or slide, etc., there are a variety of different ways in which the sample can be analyzed. For example, a chemical analysis may be performed, such as a colorimetric test. In another example, one may perform vaporization, ionization, or mass spectrometry on the sample. Also, fluorescent immunochemistry techniques may be performed to analyze the sample. The above examples are a few of the many ways in which the system may analyze the fluid sample.

As described above, the Differential Mode of the present invention permits the metering of small samples in a manner which avoids sealing problems because the diameters of the rods and the cylinders are larger than a conventional pipette that meters small samples in a Bulk Mode. However, pipettes are often grouped in a large array of perhaps 96 or 196 pipettes condensed into a block arrangement. Therefore, the present invention also seeks to compensate for the increased space or cross-sectional area that each pipette fills in order to allow a comparable number of pipettes to be arranged in a designated area, despite the larger cross-sectional area of each pipette. In one embodiment, an array of a plurality of pipettes are stacked on top of another array of a plurality of pipettes. However, they are stacked such that the passageways of the pipettes in one layer are offset from the passageways of the pipettes in another layer. In this embodiment, in addition to comprising the plurality of pipettes, the lower layer of the stack also contains channels or passageways that align with the passageways of the pipettes in the stacks above, such that the pipettes in both top and bottom layer meter fluid samples from the same level. In this way, the present invention is able to accurately meter small samples, while still permitting an equivalent number of pipettes to occupy a specified area, as compared to conventional pipettes that only operate in Bulk Mode.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A pipette module comprising:
    a channel block having at least one passage extending therethrough;
    a rod sized, shaped and aligned to pass into the channel block passage;
    a cylinder having a passage extending therethrough, the cylinder sized, shaped and aligned to pass into the channel block passage from the end opposite the end into which the rod passes;
    a chamber defined by the channel block, rod, and cylinder, having a volume which is variable during the pipetting operation of the pipette module, with a first part of the chamber variable by relative movement of the channel block relative to the fixed relative positions of the rod and cylinder, and with a second part of the chamber variable by relative movement of the cylinder relative to the fixed relative positions of the rod and channel block;
    a tip having a passageway therethrough, extending downwardly from the bottom of the cylinder; and
    an extension mandrel with a passageway extending therethrough, the mandrel attached at an end of the cylinder such that the passageway extending through the mandrel is aligned with the passage extending through the cylinder, wherein the mandrel reduces the internal volume within the tip.

2. The pipette module of claim 1, wherein the extension mandrel is removably secured to the cylinder.

3. A pipette module comprising:
    a channel block having at least one passage extending therethrough;
    a rod sized, shaped and aligned to pass into the channel block passage;
    a cylinder having a passage extending therethrough, the cylinder sized, shaped and aligned to pass into the channel block passage from the end opposite the end into which the rod passes;
    a chamber defined by the channel block, rod, and cylinder, having a volume which is variable during the pipetting operation of the pipette module, with a first part of the chamber variable by relative movement of the channel block relative to the fixed relative positions of the rod and cylinder, and with a second part of the chamber variable by relative movement of the cylinder relative to the fixed relative positions of the rod and channel block; and
    wherein the passage extending through the cylinder extends entirely through the cylinder from one end of the cylinder through to an opposite end of the cylinder.

4. The pipette module of claim 3, wherein a third part of the chamber is variable by relative movement of the rod relative to the fixed relative positions of the channel block and cylinder.

5. The pipette module of claim 4, wherein the diameter of the rod is less than the inner diameter of the channel block, providing an annular space between the inside surface of the channel block and the outside surface of the rod, defining said third part of the chamber.

6. The pipette module of claim 3, wherein the diameter of the rod is greater than the diameter of the cylinder, providing an annular space between the inner surface of the channel block and the outer surface of the cylinder, defining said first part of the chamber.

7. A pipette module comprising:
   a channel block having at least one passage extending therethrough;
   a rod sized, shaped and aligned to pass into the channel block passage;
   a cylinder having a passage extending therethrough, the cylinder sized, shaped and aligned to pass into the channel block passage from the end opposite the end into which the rod passes;
   a chamber defined by the channel block, rod, and cylinder, having a volume which is variable during the pipetting operation of the pipette module, with a first part of the chamber variable by relative movement of the channel block relative to the fixed relative positions of the rod and cylinder, and with a second part of the chamber is variable by relative movement of the cylinder relative to the simultaneously fixed relative positions of the rod and channel block.

8. The pipette module of claim 7, wherein a third part of the chamber is variable by relative movement of the rod relative to the fixed relative positions of the channel block and cylinder.

9. The pipette module of claim 8, wherein the diameter of the rod is less than the inner diameter of the channel block, providing an annular space between the inside surface of the channel block and the outside surface of the rod, defining said third part of the chamber.

10. The pipette module of claim 7, wherein the diameter of the rod is greater than the diameter of the cylinder, providing an annular space between the inner surface of the channel block and the outer surface of the cylinder, defining said first part of the chamber.

11. The pipette module of claim 7, wherein no portion of the rod extends into the passage extending through the cylinder.

12. The pipette module of claim 7, wherein at least a portion of the passage is axially extending through the cylinder.

* * * * *